(12) United States Patent
Mir et al.

(10) Patent No.: US 10,065,913 B2
(45) Date of Patent: Sep. 4, 2018

(54) UNSATURATED DEOXYBENZOIN COMPOUNDS AND POLYMERS PREPARED THEREFROM

(71) Applicant: The University of Massachusetts, Boston, MA (US)

(72) Inventors: Aabid A. Mir, Amherst, MA (US); Todd Emrick, South Deerfield, MA (US); Umesh Choudhary, Shrewsbury, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 162 days.

(21) Appl. No.: 15/286,768

(22) Filed: Oct. 6, 2016

(65) Prior Publication Data

US 2017/0101361 A1   Apr. 13, 2017

Related U.S. Application Data

(60) Provisional application No. 62/238,186, filed on Oct. 7, 2015.

(51) Int. Cl.
   *C07C 49/835* (2006.01)
   *C08G 63/00* (2006.01)
   (Continued)

(52) U.S. Cl.
   CPC ............ *C07C 49/835* (2013.01); *C07C 49/84* (2013.01); *C08G 63/00* (2013.01); *C08G 63/91* (2013.01)

(58) Field of Classification Search
   None
   See application file for complete search history.

(56) References Cited

U.S. PATENT DOCUMENTS

| 7,863,400 B2 | 1/2011 | Emrick et al. |
| 8,314,202 B2 | 11/2012 | Emrick et al. |

(Continued)

FOREIGN PATENT DOCUMENTS

JP          H02273288       11/1990

OTHER PUBLICATIONS

Ellzey et al., "Deoxybenzoin-Based Polyarylates as Halogen-Free Fire-Resistant Polymers" Macromolecules; 2006; 39; 3553-3558.

(Continued)

*Primary Examiner* — Christopher M Rodd

(74) *Attorney, Agent, or Firm* — Cantor Colburn LLP

(57) ABSTRACT

Deoxybenzoin compounds including unsaturation are disclosed. The unsaturated deoxybenxoin compounds have the structure (I), (II), or (III)

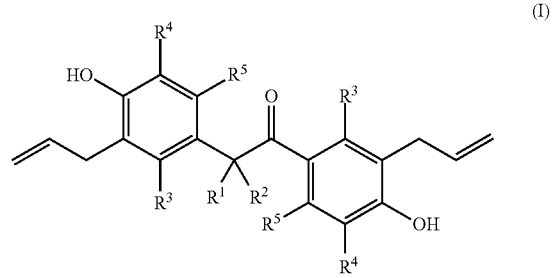

(I)

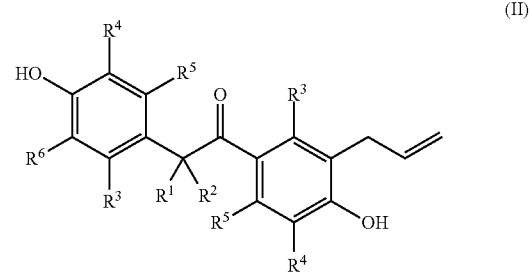

(II)

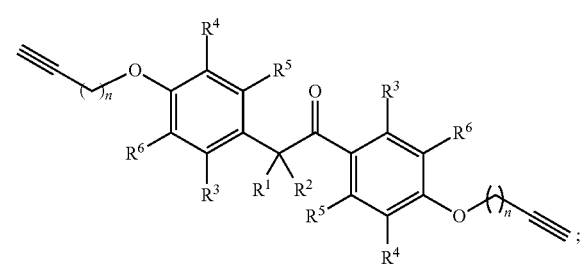

(III)

wherein $R^1$, $R^2$, $R^3$, $R^4$, $R^5$, $R^6$, and n are defined herein. Also disclosed are polyesters including repeating units having the structure (IV), (V), or a combination thereof (IV)

(Continued)

-continued

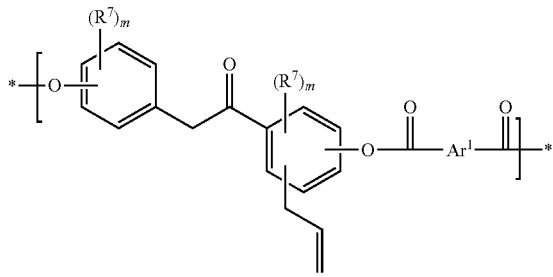

(V)

wherein $Ar^1$, $R^7$, and m are defined herein. The polyesters can be further functionalized, for example by various phosphorous-containing compounds. The polyesters described herein can be useful for the preparation of various articles having reduced flammability.

20 Claims, 5 Drawing Sheets

(51) Int. Cl.
C08G 63/91 (2006.01)
C07C 49/84 (2006.01)

(56) References Cited

U.S. PATENT DOCUMENTS

| 2011/0112241 A1* | 5/2011 | Emrick | C08G 18/10 524/549 |
|---|---|---|---|
| 2013/0102754 A1 | 4/2013 | Emrick et al. | |
| 2014/0155569 A1 | 6/2014 | Kumar et al. | |
| 2014/0357829 A1 | 12/2014 | Emrick et al. | |

OTHER PUBLICATIONS

Lyon et al., "Pyrolysis combustion flow calorimetry" J. Anal. Appl. Pyrolysis; 2004; 71; 27-46.

Walters et al., "Comparison of Heat Release Criterion for Noncombustible Materials" International SAMPE Symposium and Exhibition; 2005; 50; 1118.

* cited by examiner

UNSATURATED DEOXYBENZOIN COMPOUNDS AND POLYMERS PREPARED THEREFROM

STATEMENT REGARDING FEDERALLY SPONSORED RESEARCH & DEVELOPMENT

This invention was made with government support under grant number 14-G-012 001 awarded by the Federal Aviation Administration. The government has certain rights in the invention.

BACKGROUND OF THE INVENTION

Polymers are a mainstay of modern society, for example, widely used in fabricating textiles, upholstery, construction materials, various air, land or sea vehicles, and microelectronic devices and appliances. The inherent flammability of many polymers poses a significant threat, especially in enclosed or isolated spaces. Therefore, as synthetic polymers are used extensively in society as plastics, rubbers, and textiles, polymer flammability has been recognized as a safety hazard and remains an important challenge in polymer research.

Flame retardancy of polymers is often achieved by blending polymers with flame retardant additives, such as halocarbons, including polybrominated diphenyl ether (PBDE), phosphorus, organophosphates, and metal oxides. While small molecule flame retardant additives provide a convenient means for reducing flammability of polymers, these additives can compromise safety from environmental and health perspectives. Conventional flame retardants are small molecule additives that often leach out of the polymer during their use leading to a variety of serious health and environmental problems associated with toxicity and bioaccumulation. These concerns have led to an emphasis on non-halogenated flame retardants in recent years. However, non-halogenated flame retardant additives, such as alumina trihydrate, compromise the physical and mechanical properties of polymers when loaded at high levels.

An ideal low-flammable polymer would be halogen-free and possess high thermal stability, low heat of combustion, and a low combustion heat release rate (HRR), with minimal release of toxic fumes. Intrinsically fire-resistant polymers that undergo significant carbonization upon heating are highly desirable, as carbonaceous char formation effectively averts combustion by producing an insulating layer on the polymer surface. Such char formation can also be realized from composite materials in which an additive ultimately provides the desired char.

Aromatic polyesters prepared from bisphenols and phthalic acids are important high performance engineering thermoplastics. Conventional bisphenol A (BPA)-containing polyarylates are well-known and widely used, but exhibit higher-than-desired flammability (e.g., BPA-polyarylates have a heat release capacity (HRC) of about 400 Joules per gram-Kelvin (J/g-K)). Polyarylates containing 1,1-dichloro-2,2-bis(4-hydroxyphenyl)ethylene (bisphenol C, or BPC) are transparent and processable, and exhibit excellent mechanical and dielectric properties. BPC-containing polymers are well within the "ultra fire-resistant" category (HRC<100 J/g-K), with BPC-polyarylates and polycarbonates having reported HRC values of 21 and 29 J/g-K, respectively, and high char yields (50-55%). However, the presence of halogen in BPC-containing polymers, and the evolution of hydrogen chloride gas at elevated temperatures, remain concerns, thus limiting their adoption for scale-up and manufacturing as commodity materials.

BPC derivatives can be converted to the corresponding diphenylacetylene by loss of the chlorines, followed by phenyl migration. In BPC-containing polymers, this reaction represents a viable mechanism to char formation, in which the presence of chlorine sets up the rearrangement chemistry that leads to diphenylacetylene. In fact, diphenylacetylene-containing poly(aryl ether ketone)s showed heat release characteristics of similar magnitude to the corresponding BPC-containing polymers. However, these alkyne-containing aromatic polymers are prone to side-reactions and cross-linking even at moderately high temperatures, and have less-than-optimal processability and mechanical properties for many polymer materials applications. Accordingly, there is an ongoing search in the art for non-halogenated polymers or additives which promote charring or preclude combustion.

One approach has been the use of polyarylates incorporating a deoxybenzoin moiety, e.g., 4,4'-bishydroxydeoxybenzoin (BHDB), as a bisphenolic monomer. These polymers exhibited low combustion heat release rate and total heat of combustion, which is believed to arise from the thermally-induced conversion of BHDB to diphenylacetylene moieties that char by aromatization. See, K. A. Ellzey, T. Ranganathan, J. Zilberman, E. B. Coughlin, R. J. Farris, T. Emrick, *Macromolecules* 2006, 39, 3553. Pyrolysis combustion flow calorimetry (PCFC), an oxygen consumption technique for measuring heat release capacity (HRC), revealed exceptionally low HRC values for the BHDB-polyarylates (<100 J/g-K). See, R. N. Walters, M. Smith, and M. R. Nyden, *International SAMPE Symposium and Exhibition* 2005, 50, 1118. However, the rather low solubility of such polyarylate compounds limits their molecular weight and processibility.

Despite the ongoing interest in the field of flame retardant polymer materials, there remains a continuing need for synthetic strategies toward structurally and functionally diverse flame-retardant polymers that can overcome the above-described technical limitations.

BRIEF SUMMARY

One embodiment is an unsaturated deoxybenzoin compound having the structure (I), (II), or (III)

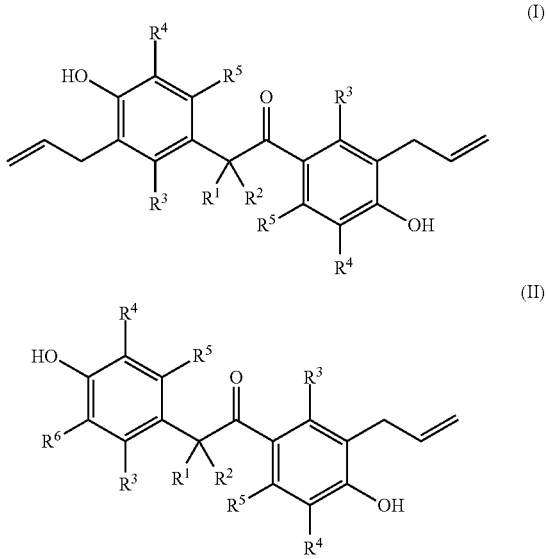

-continued

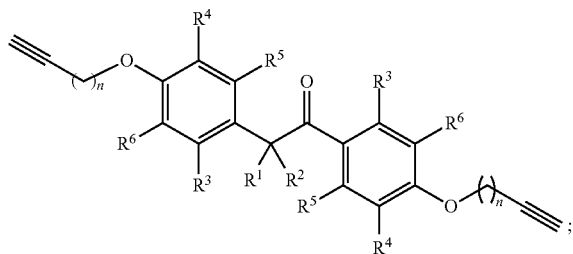

(III)

wherein $R^1$ and $R^2$ are independently at each occurrence hydrogen, a halogen, a nitrile group, a $C_{1-6}$ alkyl group, or a $C_{6-20}$ aryl group; $R^3$, $R^4$, $R^5$, and $R^6$ are independently at each occurrence hydrogen, a halogen, a hydroxyl group, a nitrile group, a $C_{1-6}$ alkyl group, a $C_{1-6}$ alkoxy group, or a $C_{6-20}$ aryl group; and n is independently at each occurrence an integer from 1 to 12.

Another embodiment is a polyester comprising repeating units having the structure (IV), (V), or a combination thereof

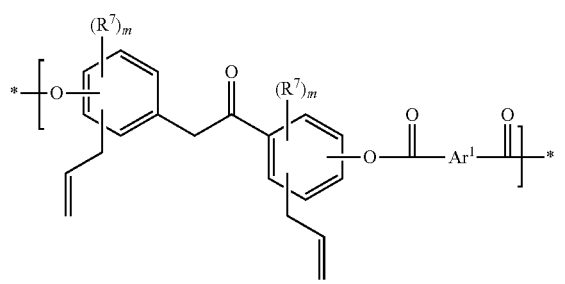

(IV)

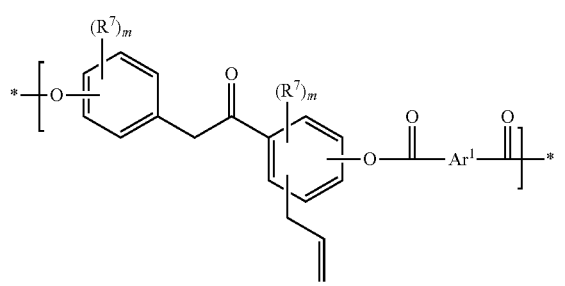

(V)

wherein $Ar^1$ is a divalent substituted or unsubstituted $C_{6-20}$ arylene group; $R^7$ is independently at each occurrence a halogen, a hydroxyl group, a nitrile group, a $C_{1-6}$ alkyl group, a $C_{1-6}$ alkoxy group, or a $C_{6-20}$ aryl group; and m is independently at each occurrence 0, 1, 2, 3, or 4.

Another embodiment is a polyester comprising repeating units having the structure (IX), (X), or a combination thereof

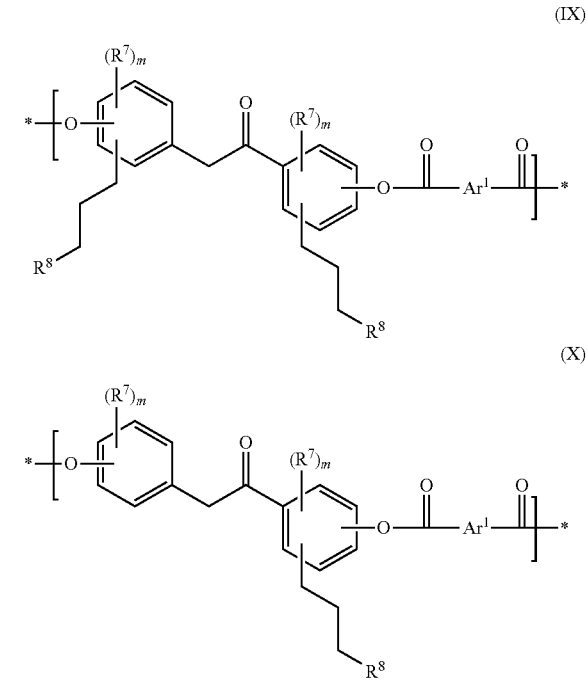

wherein $Ar^1$ is a divalent substituted or unsubstituted $C_{6-20}$ arylene group; $R^7$ is independently at each occurrence a halogen, a hydroxyl group, a nitrile group, a $C_{1-6}$ alkyl group, a $C_{1-6}$ alkoxy group, or a $C_{6-20}$ aryl group; m is independently at each occurrence 0, 1, 2, 3, or 4; and $R^8$ is a phosphorous-containing group.

Another embodiment is an article comprising one or more of the above-described polyesters.

These and other embodiments are described in detail below.

DETAILED DESCRIPTION

Figure 1:
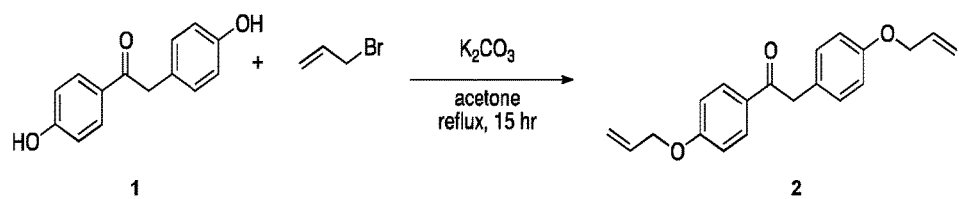
FIG. 1 is a chemical scheme illustrating the synthesis of the diallyl ether derivative of BHDB.

The present inventors have prepared new functionalized derivatives of deoxybenzoin containing unsaturation. In particular, the present inventors have prepared diallyl-, monoallyl-, and dipropargyl-containing derivatives of deoxybenzoin. These deoxybenzoin compounds advantageously include unsaturation, offering an opportunity for further functionalization. In a particularly valuable aspect, the functionalized deoxybenzoin compound can be a diallyl- or monoallyl-functionalized bisphenolic deoxybenzoin, where step growth polymerization can proceed using the phenols. The resulting polymer advantageously includes pendent allyl groups built into the polymer product (up to two per repeating unit). The pendent double bonds on the polymer chain represent reactive handles through which the polymer can be cross-linked to give a network structure, or to which the polymer can be substituted by conversion of the double bonds to other groups such as epoxides, haloalkyl groups, hydroxides, diols, or thio-ethers through the use of thiol-ene reactions. Other thiols, containing P—SH bonds, are candidates for reaction with the double bonds and are expected to contribute to further reduction of polymer heat release upon burning. Additionally, phosphite compounds can be reacted with the double bonds to provide new phosphite-functionalized polyarylates.

Polymers prepared from the allyl-functionalized bisphenolic deoxybenzoin compound can have a desirable combination of thermal properties, including reduced weight loss at elevated temperatures (e.g., 350° C. or above), low char yields, and improved heat release capacity and total heat release. Accordingly, the polymers disclosed herein represent a new class of functionalized flame retardant polymers.

One aspect of the present disclosure is an unsaturated deoxybenzoin compound having the structure (I), (II), or (III)

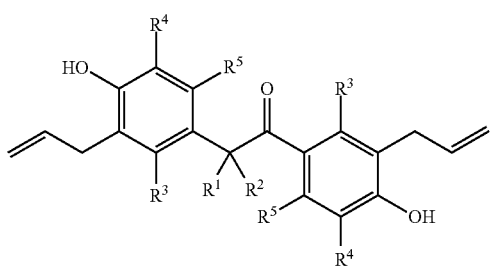

(I)

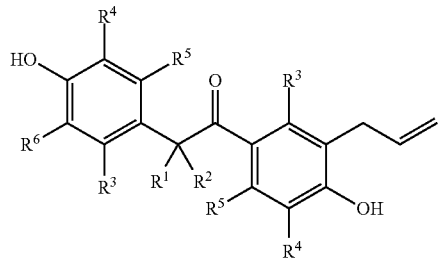

(II)

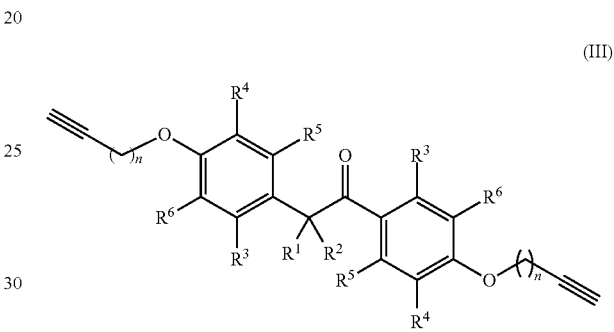

(III)

wherein $R^1$ and $R^2$ are independently at each occurrence hydrogen, a halogen, a nitrile group, a $C_{1-6}$ alkyl group, or a $C_{6-20}$ aryl group; $R^3$, $R^4$, $R^5$, and $R^6$ are independently at each occurrence hydrogen, a halogen, a hydroxyl group, a nitrile group, a $C_{1-6}$ alkyl group, a $C_{1-6}$ alkoxy group, or a $C_{6-20}$ aryl group; and n is independently at each occurrence an integer from 1 to 12 (e.g., n is independently at each occurrence 1, 2, 3, 4, 5, 6, 7, 8, 9, 10, 11, or 12). In some embodiments, each occurrence of $R^1$ and $R^2$ is hydrogen. In some embodiments, each occurrence of n is 1. In some embodiments, each occurrence of $R^3$, $R^4$, $R^5$, and $R^6$ is hydrogen.

In some embodiments, the unsaturated deoxybenzoin compound has the structure (I)

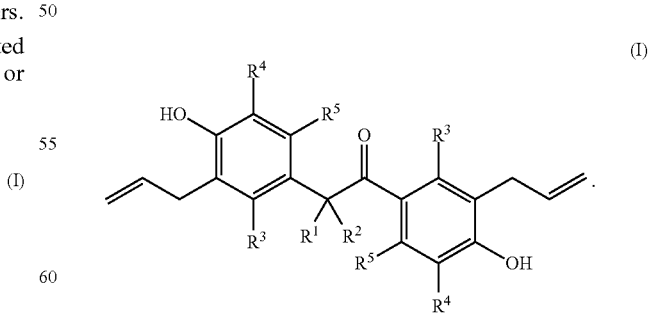

(I)

In an embodiment, the unsaturated deoxybenzoin compound has the structure (I) and each occurrence of $R^1$ and $R^2$ is hydrogen, and each occurrence of $R^3$, $R^4$, and $R^5$ is hydrogen.

In some embodiments, the unsaturated deoxybenzoin compound has the structure (II)

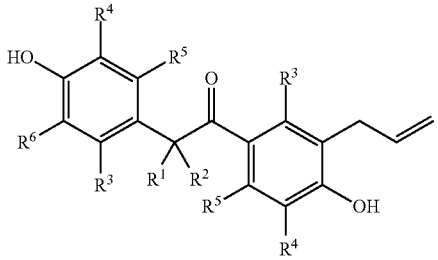
(II)

In an embodiment, the unsaturated deoxybenzoin compound has the structure (II) and each occurrence of $R^1$ and $R^2$ is hydrogen, and each occurrence of $R^3$, $R^4$, $R^5$, and $R^6$ is hydrogen.

In some embodiments, the unsaturated deoxybenzoin compound has the structure (III)

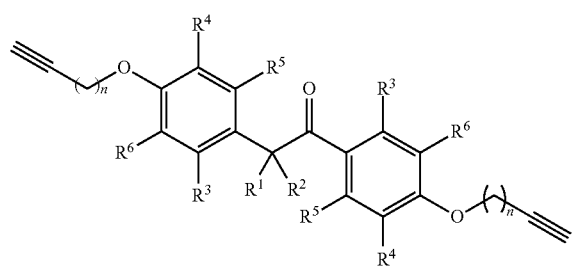
(III)

In an embodiment, the unsaturated deoxybenzoin compound has the structure (III) and each occurrence of $R^1$ and $R^2$ is hydrogen, each occurrence of n is 1 to 12, preferably 1, and each occurrence of $R^3$, $R^4$, $R^5$, and $R^6$ is hydrogen.

Another aspect of the present disclosure is a polyester comprising repeating units having the structure (IV), (V), or a combination thereof

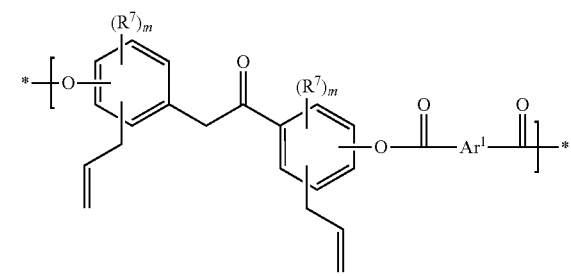
(IV)

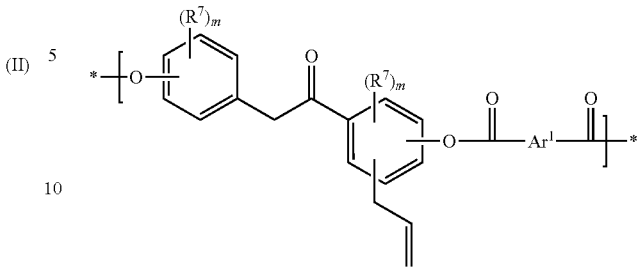
(V)

wherein $Ar^1$ is a divalent substituted or unsubstituted $C_{6-20}$ arylene group; $R^7$ is independently at each occurrence halogen, a hydroxyl group, a nitrile group, a $C_{1-6}$ alkyl group, a $C_{1-6}$ alkoxy group, or a $C_{6-20}$ aryl group; and m is independently at each occurrence 0, 1, 2, 3, or 4, provided that the valence of the phenyl group of the deoxybenzoin is not exceeded. In some embodiments, $Ar^1$ can include a substituted or unsubstituted phenylene group (e.g., a meta-phenylene group, a para-phenylene group, and the like), a phenylene oligomer (e.g., biphenylene, triphenylene, and the like), a naphthalene group, an anthracene group, a pyrene group, a perylene group, and the like, or a combination thereof. In some embodiments, $Ar^1$ can be derived from a substituted or unsubstituted $C_{6-20}$ aromatic dicarboxylic acid or a derivative thereof (e.g., the corresponding acid halide). For example, $Ar^1$ can be derived from isophthalic acid, terephthalic acid, naphthalene dicarboxylic acids, 1,2-di(p-carboxyphenyl)ethane, 4,4'-dicarboxydiphenyl ether, 4,4'-bisbenzoic acid, and combinations thereof. In some embodiments, $Ar^1$ is derived from terephthalic acid, isophthalic acid, naphthalene dicarboxylic acids, or a combination thereof. In some embodiments, $Ar^1$ is derived from isophthalic acid or terephthalic acid, and $Ar^1$ is a phenylene group. In some embodiments, m is 0. In some embodiments, the allyl group is preferably positioned ortho to the ester linkages of the polyester backbone.

In some embodiments, the polyester comprises repeating units according to structure (IV), wherein m is 0 and the allyl group is positioned ortho to the ester linkage of the polymer backbone. For example, the polyester can comprise repeating units according to formula (VI)

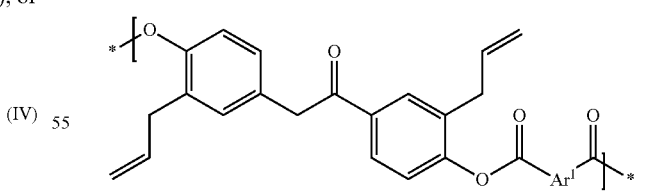
(VI)

wherein $Ar^1$ is a divalent substituted or unsubstituted $C_{6-20}$ arylene group, preferably a phenylene group. In some embodiments, $Ar^1$ can be derived from isophthalic acid, terephthalic acid, or a combination thereof. In some embodiments, where $Ar^1$ of the polyester according to formula (VI) is a phenylene group derived from isophthalic acid, the polyester can comprise repeating units having the structure (VIA)

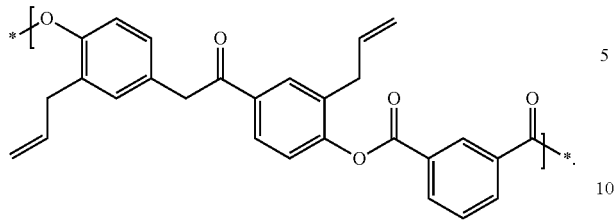

(VIA)

In some embodiments, the polyester comprises repeating units according to structure (V), wherein m is 0 and the allyl groups are positioned ortho to the ester linkage of the polymer backbone. For example, the polyester can comprise repeating units according to formula (VIII)

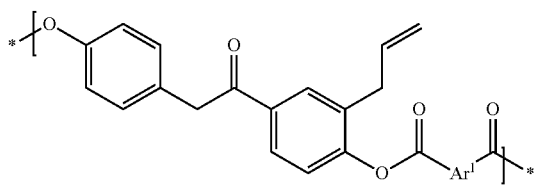

(VIII)

wherein $Ar^1$ is a divalent substituted or unsubstituted $C_{6-20}$ arylene group, preferably a phenylene group. In some embodiments, $Ar^1$ can be derived from isophthalic acid, terephthalic acid, or a combination thereof. In some embodiments, where $Ar^1$ of the polyester according to formula (VIII) is a phenylene group derived from isophthalic acid, the polyester can comprise repeating units having the structure (VIIIA)

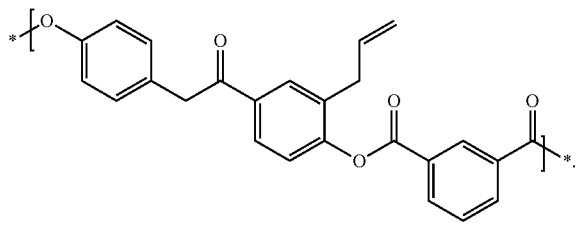

(VIIIA)

In some embodiments, the polyester can be a copolyester. The copolyester can be a random or block copolyester. In some embodiments, the copolyester comprises repeating units according to structure (IV) and (V).

In some embodiments, the polyester can be a copolyester comprising repeating units according to structures (IV), (V), or a combination thereof, and further comprising repeating units according to structure (VII)

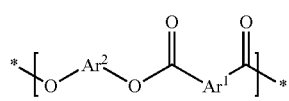

(VII)

wherein $Ar^1$ can be as described above, and $Ar^2$ is a substituted or unsubstituted $C_{6-30}$ arylene group. In some embodiments, exemplary $Ar^2$ groups can be of the formula

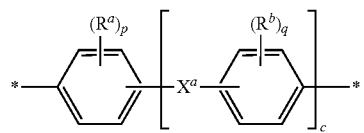

wherein $R^a$ and $R^b$ are each independently the same or different, and are a halogen atom or a monovalent $C_{1-6}$ alkyl group; p and q are each independently integers of 0 to 4 (e.g., 0, 1, 2, 3, or 4); c is 0 to 4 (e.g., 0, 1, 2, 3, or 4); and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. The group $Ar^2$ can be derived from the corresponding dihydroxy compound. A specific example of an $Ar^2$ group is a divalent group of the formula

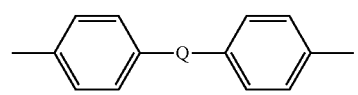

wherein Q is —O—, —S—, —C(O)—, —SO$_2$—, —SO—, or —C$_y$H$_{2y}$— wherein y is an integer from 1 to 5 or a halogenated derivative thereof (including a perfluoroalkylene group). In some embodiments, $Ar^2$ is a biphenyl group, for example 4,4'-dihydroxybiphenyl and the like. In some embodiments, $Ar^2$ can be derived from a bisphenol compound, for example bisphenol A, bisphenol C, bisphenol F, bisphenol AC, and the like. In a specific embodiment $Ar^2$ is a derived from bisphenol A, such that Q in the above formula is 2,2-isopropylidene. In some embodiments, exemplary $Ar^2$ groups can further include those of the formula

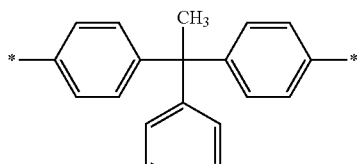

and

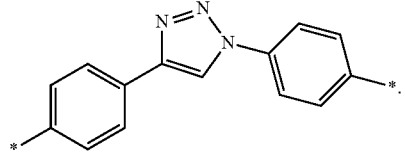

In some embodiments, the polyester is a copolymer further comprising repeating units derived from 2,2-bis(4-hydroxyphenyl)propane (bisphenol A). Stated another way, the copolymer can further comprise repeating units according to structure (VII) above, wherein $Ar^2$ is 4,4'-diphenylene isopropylidene. For example, the copolymer further comprises repeating units of the formula (VIIA)

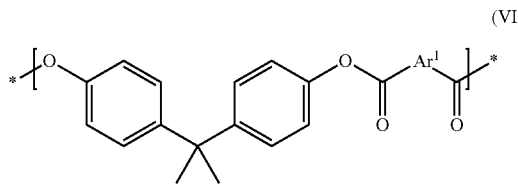

(VIIA)

wherein $Ar^1$ is as described above, and is preferably phenylene.

In some embodiments, the polyester of the present disclosure can have a number average molecular weight of 1,000 to 100,000 Daltons (Da), for example 5,000 to 75,000 Da, for example 10,000 to 50,000 Da. The molecular weight of the polymer can be determined according to techniques that are generally known, for example using gel permeation chromatography (GPC).

In an embodiment, the polyester comprises repeating units of formula (VI)

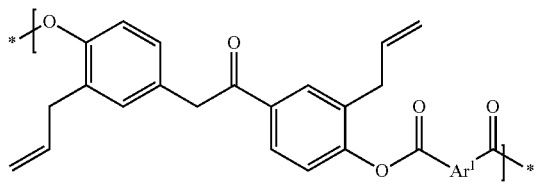

(VI)

wherein $Ar^1$ is a divalent phenylene group; and the polyester has a number average molecular weight of 10,000 to 100,000 Daltons. In a specific embodiment, the polyester comprises repeating units of formula (IVA)

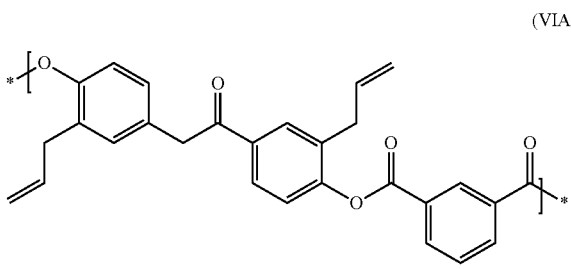

(VIA)

wherein the polyester has a number average molecular weight of 10,000 to 100,000 Daltons.

In another embodiment, the polyester is a copolyester comprising repeating units of formulas (VI) and (VII)

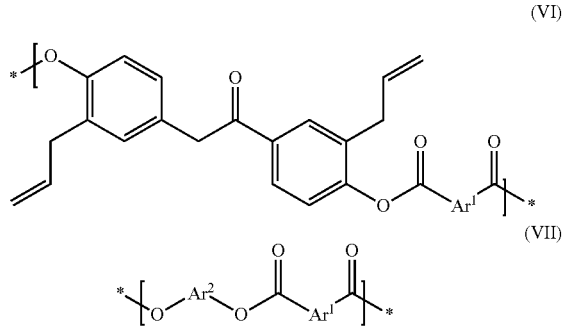

(VI)

(VII)

wherein $Ar^1$ is a divalent phenylene group, $Ar^2$ is 4,4'-diphenylene isopropylidene, and the copolyester has a molecular weight of 10,000 to 100,000 Daltons. In a specific embodiment, the polyester is a copolyester comprising repeating units of formulas (VIA) and (VIIB)

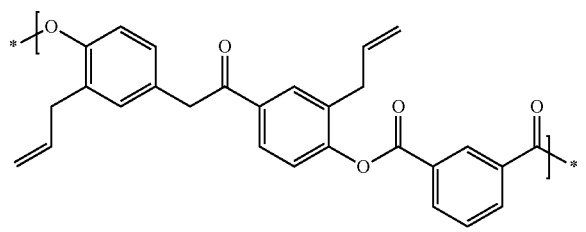

(VIA)

(VIIB)

wherein the copolyester has a number average molecular weight of 10,000 to 100,000 Daltons.

In an embodiment, the polyester comprises repeating units of formula (VIII)

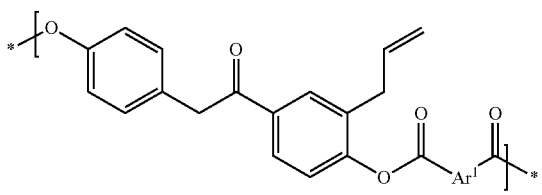

(VIII)

wherein $Ar^1$ is a divalent phenylene group; and the polyester has a number average molecular weight of 10,000 to 100,000 Daltons. In a specific embodiment, the polyester comprises repeating units of formula (VIIIA)

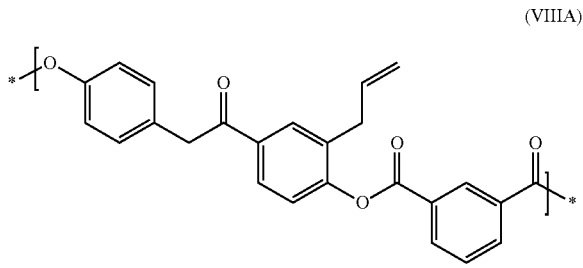

(VIIIA)

wherein the polyester has a number average molecular weight of 10,000 to 100,000 Daltons.

In another embodiment, the polyester is a copolyester comprising repeating units of formulas (VIII) and (VII)

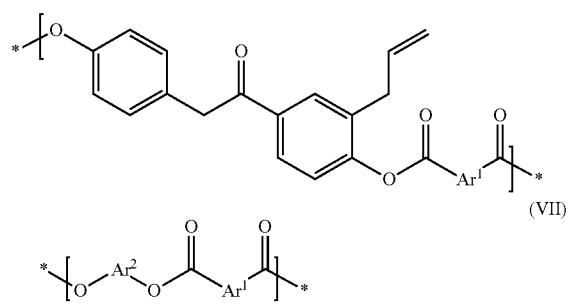

(VIII)

(VII)

wherein $Ar^1$ is a divalent phenylene group, $Ar^2$ is 4,4'-diphenylene isopropylidene, and the copolyester has a molecular weight of 10,000 to 100,000 Daltons. In a specific embodiment, the polyester is a copolyester comprising repeating units of formulas (VIIIA) and (VIIB)

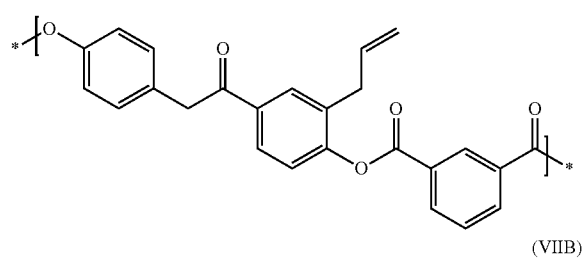

(VIIIA)

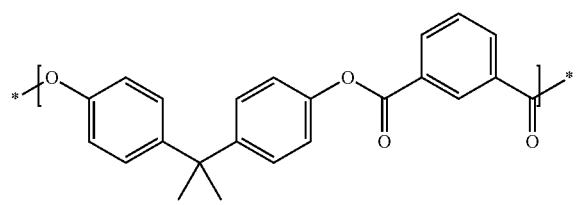

(VIIB)

wherein the copolyester has a number average molecular weight of 10,000 to 100,000 Daltons.

In another aspect of the present disclosure, the above-described allyl-functionalized polyesters can be particularly useful for incorporating various functional groups, for example using post-polymerization functionalization of the allyl groups. Exemplary groups that can be incorporated to the polymer structure via reaction with the allyl groups can include, for example, phosphorous-containing compounds (e.g., phosphites). Accordingly, another aspect of the present disclosure is a copolyester comprising repeating units having the structure (IX), (X), or a combination thereof

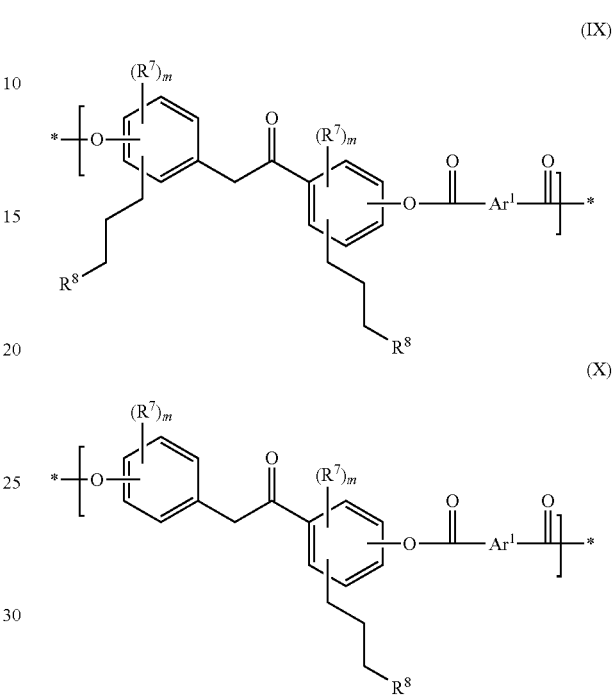

(IX)

(X)

wherein $Ar^1$ is a divalent substituted or unsubstituted $C_{6-20}$ arylene group; $R^7$ is independently at each occurrence a halogen, a hydroxyl group, a nitrile group, a $C_{1-6}$ alkyl group, a $C_{1-6}$ alkoxy group, or a $C_{6-20}$ aryl group; m is independently at each occurrence 0, 1, 2, 3, or 4; and $R^8$ is a phosphorous-containing group. In some embodiments, the phosphorous-containing group can be, for example,

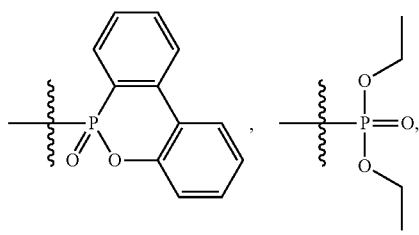

and the like, or a combination thereof. The phosphorous-containing groups can be incorporated into the polyester via the allyl groups using methods that are generally known, for example, using thermally initiated radical coupling. An example of the preparation of such materials is further described in the working examples below.

In some embodiments, the polyesters described herein exhibit one or more advantageous thermal properties. For example, the polyesters are stable to temperatures of at least 350° C., or at least 360° C., or at least 380° C., or at least 400° C. The thermal stability of the polymers can be assessed using thermogravimetric analysis, which indicates the onset of degradation (indicated by weight loss) at temperatures of at least 350° C., for example, 350 to 400° C.

For example, the polyester can exhibit a five percent weight loss temperature (i.e., temperature at which 5% of the initial weight of the sample is lost) of greater than or equal to 350° C., determined using thermogravimetric analysis, for example using a heating rate of 20° C. per minute. In some embodiments, the five percent weight loss temperature can be greater than or equal to 370° C., as determined according to thermogravimetric analysis. In some embodiments, the five percent weight loss temperature can be greater than or equal to 400° C., as determined according to thermogravimetric analysis. In some embodiments, the polyester has a weight loss of less than or equal to five weight percent after 60 minutes at 350° C., or at 370° C., or at 400° C. The polyester can further have a char yield of at least 35 percent, or at least 37 percent, or least 40 percent after 60 minutes at 750° C., as determined by thermogravimetric analysis; a heat release capacity (HRC) of less than or equal to 150 joules per gram-Kelvin determined using a pyrolysis combustion flow calorimeter; and a total heat release (THR) of less than 15 kilojoules per gram determined using a pyrolysis combustion flow calorimeter. In some embodiments, the polyester exhibits at least two of the foregoing thermal properties. In some embodiments, the polyester exhibits at least three of the foregoing thermal properties. In some embodiments, the polyester exhibits each of the foregoing thermal properties.

Describing these systems in terms of HRC eliminates the reliance on heating rate that is typical of standard flammability measurements (i.e. heat release rate), rendering it a material dependent property. THR is the total heat of complete combustion of the pyrolysis products per mass of sample used in the measurement. Lower HRC and THR values are thus good indicators of increasing the flame retarding property of the polymer.

The polyesters of the present disclosure can be prepared using techniques that are generally known. For example, the polyester can be prepared by contacting the diallyl- or monoallyl-substituted deoxybenzoin bisphenol (e.g., the deoxybenzoin compound according to structure (I) or (II)) and optionally, one or more additional dihydroxy aromatic compounds with an aromatic dicarboxylic acid, or a reactive derivative thereof (e.g., the corresponding aromatic dicarboxylic acid halide) in the presence of a solvent and under conditions effective to provide the polyester. Conditions effective to provide the polyester can include a temperature of 35 to 110° C. and a time of 10 minutes to 1 hour, or 15 to 45 minutes. An example of the preparation of the polyesters described herein is provided in the working examples below.

The compounds and materials, along with the synthetic methodologies disclosed herein can have broad impact on such diverse fields of fabricating textiles, upholstery, construction materials, various air, land or sea vehicles, and microelectronic devices and appliances. Thus, another aspect of the present disclosure is an article comprising the above-described polyester. In general the article can be any article that can benefit from the reduced flammability of the polymer material disclosed herein. In some embodiments, the article can be a fiber, a textile, a foam, a furniture component, construction materials (e.g., insulation), a vehicle component (e.g., an automobile component, a railway vehicle component, a marine vehicle component, an airplane component, and the like), an electronic component, an adhesive, a foam, paint, or a plastic.

The invention is further illustrated by the following non-limiting examples.

EXAMPLES

Experimental details for the synthesis of a diallyl-bishydroxydeoxybenzoin are provided below.

Figure 2:
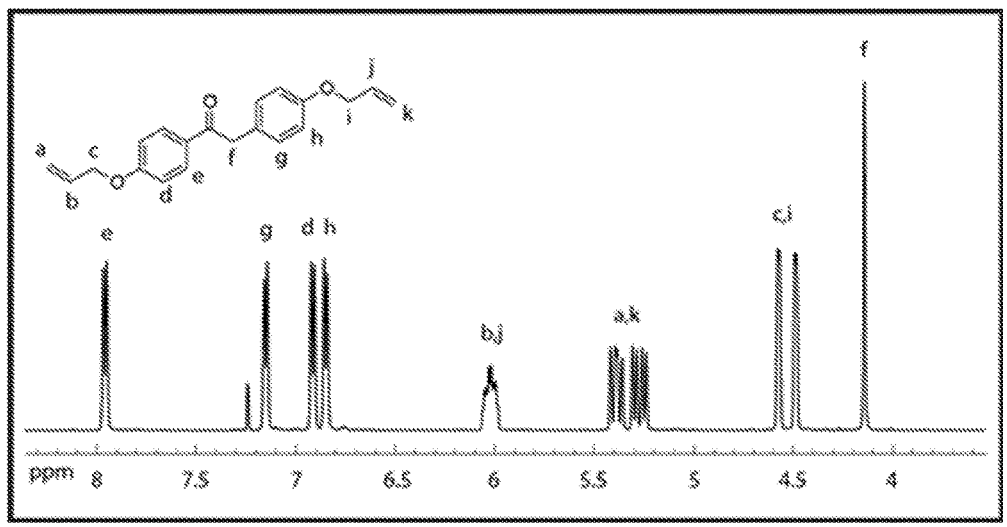
FIG. 2 is a proton nuclear magnetic resonance ($^1$H NMR) spectrum of the diallyl ether derivative of BHDB.

The diallyl ether of 4,4'-bishydroxydeoxybenzoin (BHDB), shown as compound 2 in FIG. 1, was prepared according to the following procedure. BHDB (25 grams, 110 millimoles), shown as compound 1 of FIG. 1, was dissolved in acetone (1 liter). Potassium carbonate (42.6 grams, 307 millimoles) was added, followed by allyl bromide (20 milliliters). The solution was heated to reflux for 12 hours, then allowed to cool to room temperature. Water (about 1 liter) was added until a precipitate formed. This product was filtered, dried, and recrystallized from methanol to yield off-white crystals (melting point: 83-85° C.); Proton nuclear magnetic resonance ($^1$H-NMR) spectrum (CDCl$_3$, 500 megahertz (MHz)): δ 7.91 (2H, d, J=9, Ar—H); 7.10 (2H, d, J=8.5, Ar—H); 6.87 (2H, d, J=9, Ar—H); 6.80 (2H, d, J=8.5, Ar—H); 5.96 (2H, m, CH=CH$_2$); 5.36 (2H, m, CH$_2$=CH); 5.25 (2H, m, CH$_2$=CH); 4.52 (2H, d, J=5); 4.43 (2H, d, J=5.5); 4.09 (2H, s, Ar—CO—CH$_2$—Ar). The $^1$H NMR spectrum is shown as FIG. 2. $^{13}$Carbon ($^{13}$C) NMR spectrum (CDCl$_3$, 500 megahertz (MHz)): δ 196.63, 162.68, 157.65, 133.48, 132.67, 131.04, 129.95, 127.24, 118.27, 117.24, 115.01, 68.98 (O—*CH$_2$—CH=CH$_2$), 44.54.

Figure 3:
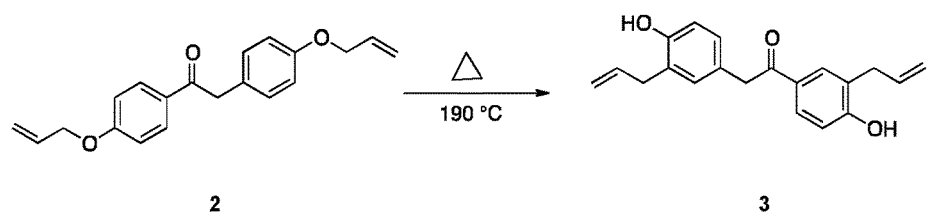
FIG. 3 is a chemical scheme illustrating the synthesis of a diallyl-functionalized bisphenolic deoxybenzoin.
Figure 4:
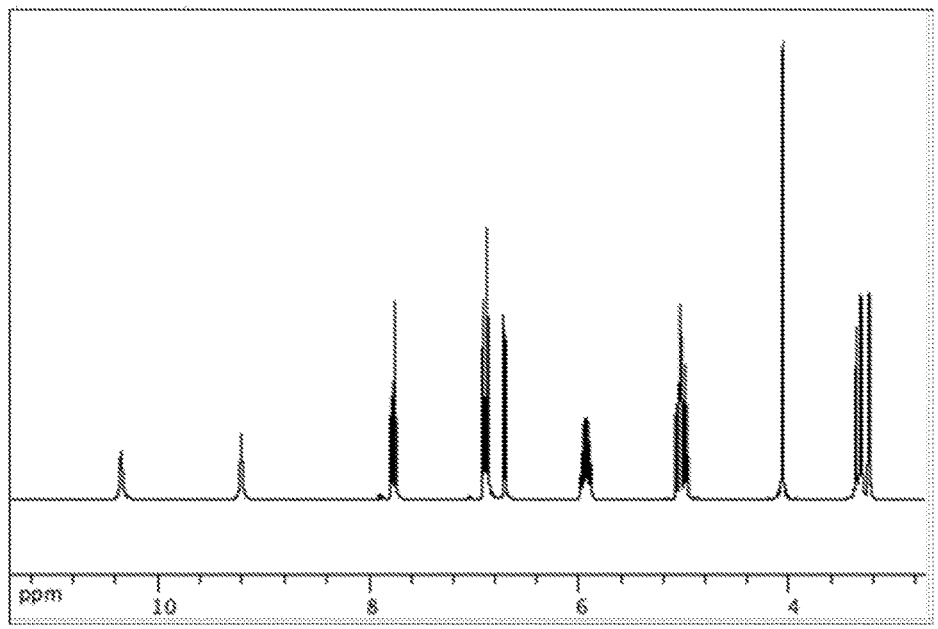
FIG. 4 is a $^1$H NMR spectrum of the diallyl-functionalized bisphenolic deoxybenzoin.

1,2-Bis(3-allyl-4-hydroxyphenyl)ethanone, shown as compound 3 in FIG. 3, was synthesized according to the following procedure. Compound 2 (10 grams, 0.032 moles) was heated to 170-190° C. for 18 hours in a nitrogen atmosphere, then cooled to ambient temperature to give a brown oil (9.5 grams, 95% yield). $^1$H-NMR (DMSO, 500 Mhz): δ 10.35 (s, 1H, OH, Ar—CO), 9.21 (s, 1H, OH—Ar—CH$_2$), 7.74 (d, 2H), 6.86-6.91 (m, 3H, Ar—H), 6.71 (d, 1H), 5.95 (m, 2H, CH), 5.02 (m, 4H, 2-CH$_2$), 4.05 (s, 2H, Ar—CO—CH$_2$—Ar), 3.22-3.31 (dd, 4H, J$_1$=7, J$_2$=6.5, Ar—CH$_2$). Mass spectrometry: (m/z) calculated for C$_{20}$H$_{20}$O$_3$: 308.37. found 308.14. The $^1$H-NMR spectra of compound 3 is shown in FIG. 4. $^{13}$C NMR spectrum (CDCl$_3$, 500 megahertz (MHz)): δ 196.63, 162.68, 157.65, 133.48, 132.67, 131.04, 129.95, 127.24, 118.27, 117.24, 115.01, 68.98 (0-*CH$_2$—CH=CH$_2$), 44.54.

Figure 5:
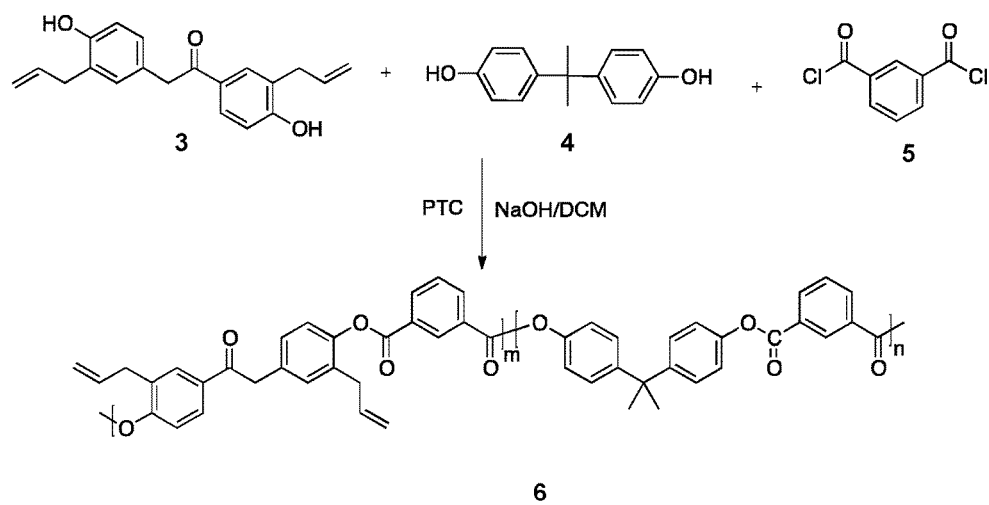
FIG. 5 is a chemical scheme illustrating the polymerization of the diallyl-functionalized bisphenolic deoxybenzoin.

A polymerization procedure for producing aromatic polyesters from diallyl-BHDB (3) is illustrated by FIG. 5, and further described by the following Examples.

Example 1

Figure 6:
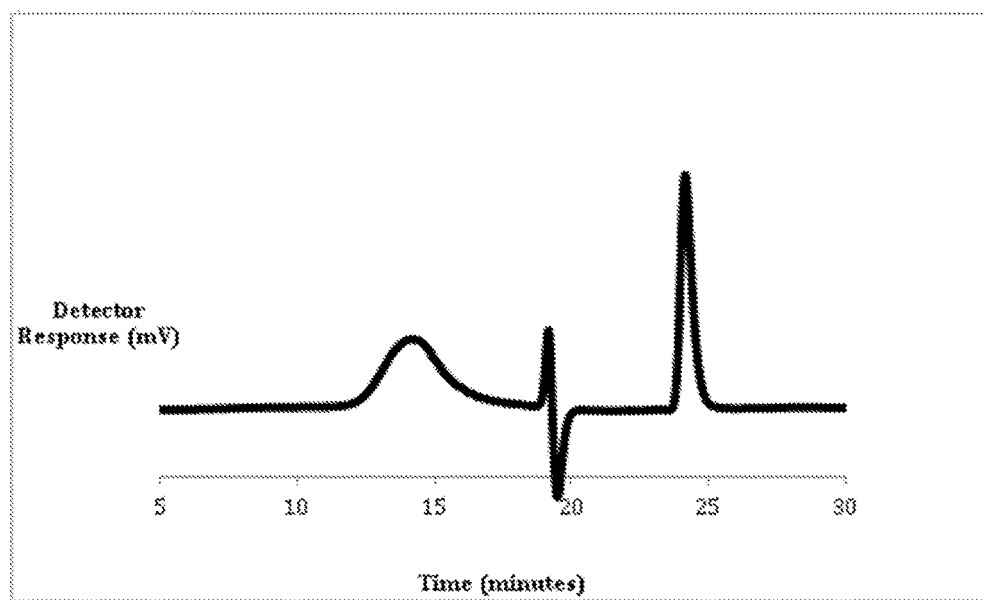
FIG. 6 is a gel permeation chromatogram (GPC) of a polymer having repeat units derived from the diallyl-functionalized bisphenolic deoxybenzoin and bisphenol A in a 50:50 molar ratio. GPC was performed in dimethylformamide using poly(methyl methacrylate) (PMMA) standards.

In a two-neck flask, an aqueous solution of sodium hydroxide (NaOH) (2.1 millimoles) in water (3 milliliters) was combined with bisphenol A (shown as compound 4) (0.5 millimoles, 114 milligrams) and diallyl-BHDB (0.5 millimoles, 154 milligrams). To this solution was added benzyltriethylammonium chloride (2.1 millimoles) and isophthaloyl chloride (shown as compound 6) (1 millimoles, 203 milligrams) in dichloromethane (3 milliliters). The mixture was stirred vigorously for 30 minutes at room temperature, at which point the organic phase became viscous. The mixture was poured into methanol (100 milliliters) to precipitate the polymer product (shown as polymer 6). The isolated polymer was purified further by soxhlet extractor, then filtered and dried overnight in a vacuum oven at 60° C. (yield=0.330 grams, 82.9%). $^1$H-NMR (500 MHz, CDCl$_3$): δ 8.93 (s, 2H, isophthaloyl aromatic), 8.35 (m, 4H, isophthaloyl aromatic), 7.92 (d, 2H, J=9.5 Hz, Ar—H), 7.60 (m, 2H, isophthaloyl aromatic), 7.02-7.28 (m, 12H, Ar—H), 5.84, (m, 2H, CH=CH$_2$), 4.96 (m, 4H, CH$_2$=CH), 4.22 (s, 2H, Ar—CO—CH$_2$—Ar), 3.37 (d, 2H, J=6.5 Hz, CH$_2$—Ar), 3.29 (d, 2H, J=6 Hz, CH$_2$—Ar), 1.66 (s, 6H, Ar—C(CH$_3$)$_2$—Ar. Gel permeation chromatography (GPC): M$_n$=17,200 Daltons; M$_w$=47,100 Daltons; PDI=2.73. The GPC chromatogram is shown as FIG. 6.

Example 2

Figure 7:
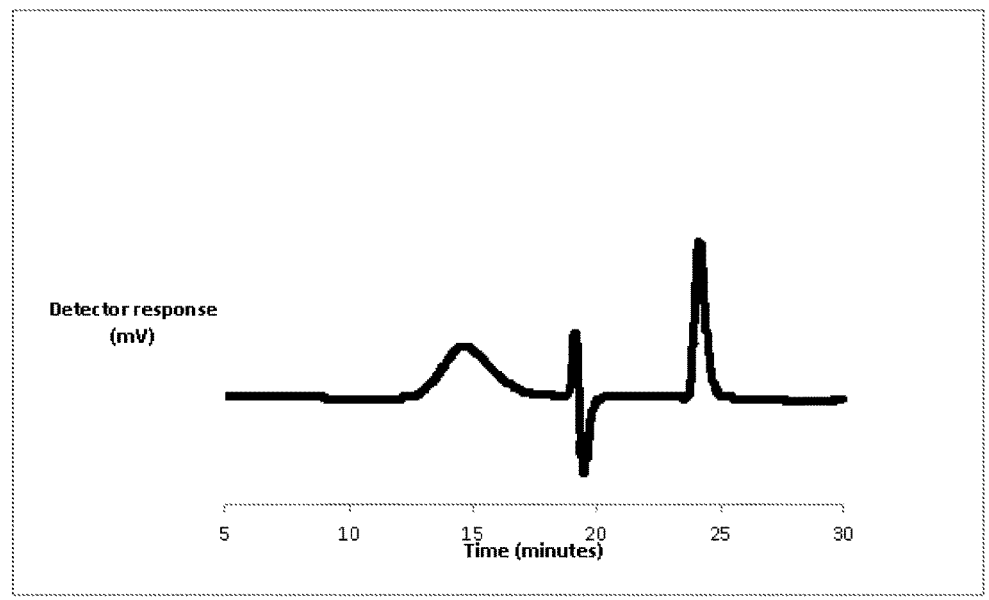
FIG. 7 is a gel permeation chromatogram (GPC) of a polymer having repeat units derived from the diallyl-functionalized bisphenolic deoxybenzoin and bisphenol A in a 70:30 molar ratio. GPC was performed in dimethylformamide using poly(methyl methacrylate) (PMMA) standards.

Isophthaloyl chloride (0.20 grams, 1.0 millimoles) was polymerized with compound 3 (0.215 grams, 0.70 millimoles) and bisphenol A (0.068 grams, 0.30 millimoles) using the same general procedure as in Example 1 to afford the polymer product as a white fibrous film (0.31 grams, 75% yield). $^1$H-NMR (500 MHz, CDCl$_3$): δ 8.92 (s, 2H, isophthaloyl aromatic), 8.41 (m, 4H, isophthaloyl aromatic), 7.93 (d, 2H, J=9.5 Hz, Ar—H), 7.61 (m, 2H, isophthaloyl aromatic), 7.02-7.28 (m, 12H, Ar—H), 5.83, (m, 2H, CH=CH$_2$), 4.99 (m, 4H, CH$_2$=CH), 4.22 (s, 2H, Ar—CO—CH$_2$—Ar), 3.39 (d, 2H, J=6.5 Hz, CH$_2$—Ar), 3.30 (d, 2H, J=6 Hz, CH$_2$—Ar), 1.65 (s, 6H, Ar—C(CH$_3$)$_2$—Ar. GPC: M$_n$=12,457; M$_w$=28,816, PDI=2.30. The GPC chromatogram is shown as FIG. 7.

Example 3

Figure 8:
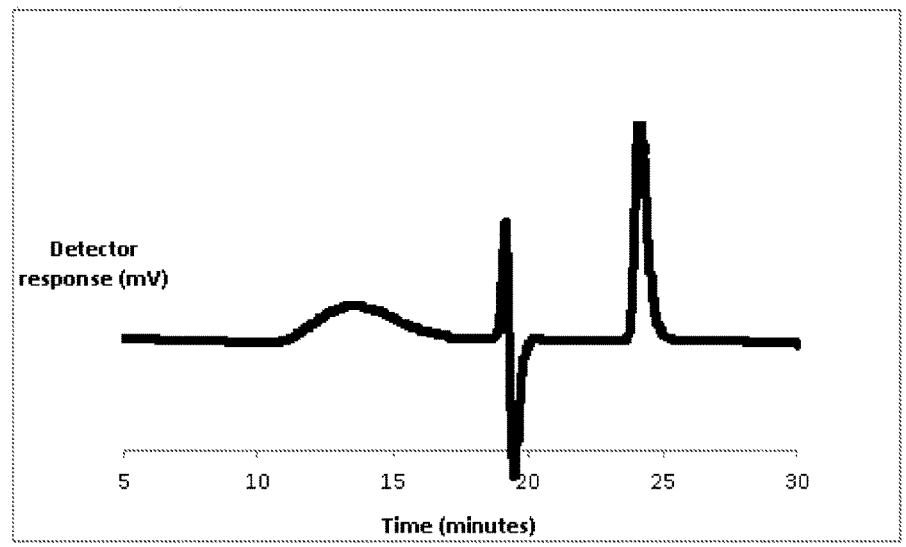
FIG. 8 is a gel permeation chromatogram (GPC) of a homopolymer having repeat units derived from the diallyl-functionalized bisphenolic deoxybenzoin. GPC was performed in dimethylformamide using poly(methyl methacrylate) (PMMA) standards.

Isophthaloyl chloride (0.1 grams, 0.5 millimoles) was polymerized with compound 3 (0.154 grams, 0.5 millimoles) using the same general procedure as in Example 1 to give white fibrous polymer (0.14 grams, 64% yield). $^1$H-NMR (500 MHz, CDCl$_3$): δ 8.93 (s, 1H, isophthaloyl aromatic), 8.38 (m, 2H, isophthaloyl aromatic), 7.92 (d, 2H, J=9.5 Hz, Ar—H), 7.63 (m, 1H, isophthaloyl aromatic), 7.11-7.25 (m, 4H, Ar—H), 5.82, (m, 2H, CH=CH$_2$), 4.95 (m, 4H, CH$_2$=CH), 4.22 (s, 2H, Ar—CO—CH$_2$—Ar), 3.36 (d, 2H, J=6.5 Hz, CH$_2$—Ar), 3.29 (d, 2H, J=6 Hz, CH$_2$—Ar). GPC: M$_n$=23800, M$_w$=80500, PDI=3.38. The GPC chromatogram is shown as FIG. 8.

Example 4

Terepthaloyl chloride (100 milligrams, 0.50 millimoles) was polymerized with compound 3 (0.154 grams, 0.50 millimoles) using the same general procedure as in Example 1 to afford a white fibrous polymer (0.20 grams, 91% yield). The polymer was isolated by precipitation into methanol. The resulting polymer was insoluble in DMF, THF and trifluoroethanol.

The diallyl-BHDB homopolymers and diallyl-BHDB copolymers with bisphenol A (BPA) of Examples 1-4 having varying molecular weight and compositions are shown in Table 1. "Feed" refers to the molar ratio of BHDB to BPA based on the total moles of bisphenol components. Incorporation of BHDB and BPA into the polymer product was characterized using proton nuclear magnetic resonance ($^1$H NMR) spectroscopy, and is reported as the molar ratio of BHDB to BPA, based on the total moles of BHDB and BPA. Number average molecular weight (Mn), weight average molecular weight (Mw), and polydispersity index (PDI) were determined by gel permeation chromatography (GPC) relative to poly(methyl methacrylate) (PMMA) standards eluting with dimethyl formamide (DMF). Molecular weights are reported in Daltons (Da). The 5 percent weight loss temperature (reported in ° C.) was determined using thermogravimetric analysis performed under nitrogen on a Q500 (TA Instruments) at a heating rate of 20° C. per minute. Char yields were also determined by TGA, taken from the mass residue at 750° C. Heat release capacity (HRC, J/(g-K)), and total heat release (THR, kJ/g) were measured on a microscale combustion calorimeter (MCC). MCC operates as a pyrolysis combustion flow calorimeter (PCFC), and was conducted from 80 to 750° C. at a heating rate of 1° C. per second in an 80 cm$^3$/minute stream of nitrogen. The anaerobic thermal degradation products in the nitrogen gas stream were mixed with a 20 cm$^3$/min stream of oxygen prior to entering the combustion furnace (900° C.). Heat release is quantified by standard oxygen consumption methods typical to PCFC. (See, e.g., Lyon, et al. 2004 J Anal Appl Pyrol 71(1):27-46; ASTM. Standard Test Method for Determining Flammability Characteristics of Plastics and Other Solid Materials Using Microscale Combustion calorimetry. ASTM D7309-13. West Conshohocken, Pa.: ASTM International, 2013, p. 11.) During the test, the heat release rate (HRR) is obtained from dQ/dt at each time interval, taking into account the initial sample mass (~5 milligrams). The HRC is obtained by dividing the maximum HRR by the heating rate.

As shown in Table 1, copolyesters can be prepared having varying ratios of dially-BHDB and BPA as comonomers (Example 1 and 2). These copolyesters exhibited good solubility in DMF, dichloromethane, chloroform, and N-methyl pyrrolidone. The copolyesters advantageously exhibited five percent weight loss temperatures of 400° C. (Example 1) and 417° C. (Example 2) as determined by TGA. Example 3 demonstrates that polyesters can be prepared from only the diallyl-BHDB monomer as the bishydroxy component. The polyester of Example 3 exhibited a number average molecular weight of 23,800 Da, determined by GPC. The polyester was also soluble in common organic solvents including DMF, NMP dichloromethane, and chloroform. The Example 3 polyester exhibited a five percent weight loss temperature of 395° C., a slightly increased char yield of 43% relative to the copolyesters of Examples 1 and 2 (37 and 40%, respectively). Furthermore, the heat release capacity and the total heat release of Example 3 were reduced (146 J/g-K and 13 kJ/g, respectively), compared to Examples 1 and 2. Example 4 demonstrates the synthesis of a homopolyester prepared from the reaction of the diallyl-BHDB monomer and terephthalic acid (compared to isophthalic acid used for Examples 1-3). This polymer of Example 4 was generally insoluble, however also exhibited beneficial thermal properties, as shown in Table 1.

TABLE 1

| | Composition | | | | | 5% wt. | | Thermal Characterization | | |
| | (BHDB:BPA) | | GPC | | | loss T | $T_g$ | Char | HRC | THR |
| Example | Feed | Incorporated | Mn | Mw | PDI | (° C.) | (° C.) | (%) | (J/g-K) | (kJ/g) |
| 1 | 50:50 | 48.24:51.76 | 17,200 | 47,100 | 2.73 | 400 | 135 | 37 | 150 | 14 |
| 2 | 70:30 | 68.75:31.25 | 12,400 | 28,800 | 2.30 | 417 | 103 | 40 | 147 | 13 |

TABLE 1-continued

| Example | Composition (BHDB:BPA) Feed | Composition (BHDB:BPA) Incorporated | GPC Mn | GPC Mw | GPC PDI | 5% wt. loss T (° C.) | Thermal Characterization $T_g$ (° C.) | Thermal Characterization Char (%) | Thermal Characterization HRC (J/g-K) | Thermal Characterization THR (kJ/g) |
|---|---|---|---|---|---|---|---|---|---|---|
| 3 | 100:0 | 100 | 23,800 | 80,500 | 3.38 | 395 | 117 | 43 | 146 | 13 |
| 4 | 100:0 | 100 | | | | 371 | 123 | 41 | 122 | 11 |

Example 5

Experimental details for the synthesis of a monoallyl-bishydroxydeoxybenzoin are provided below.

Figure 9:
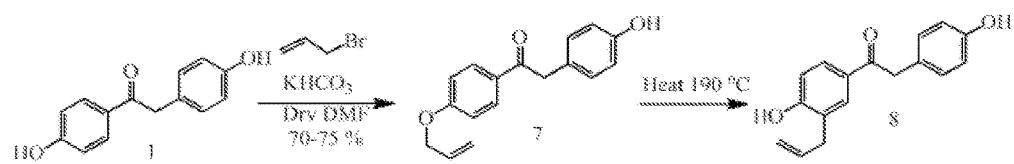
FIG. 9 is a chemical scheme illustrating the synthesis of a monoallyl-functionalized bisphenolic deoxybenzoin.

The monoallyl ether of 4,4'-bishydroxydeoxybenzoin (BHDB), shown as compound 7 in FIG. 9, was prepared according to the following procedure. BHDB (2 grams, 8.76 millimoles), shown as compound 1 of FIG. 9, was dissolved in anhydrous N,N-dimethylformamide (10 milliliters). Potassium bicarbonate (8.77 grams, 87.6 millimoles) was added, followed by allyl bromide (2.12 grams, 17.5 millimoles) over a period of about 30 minutes. The resulting solution was stirred for 50 hours at room temperature (until BHDB starting material was observed to be consumed). Water (20 milliliters) was added to precipitate the product. This product was filtered and crystallized from dichloromethane/hexane (30/70) to yield an off-white solid in 70% yield (0.188 grams) having a melting point: 80-81° C.). Proton nuclear magnetic resonance ($^1$H-NMR) spectrum (CDCl$_3$, 500 megahertz (MHz)): δ 8.00 (2H, d, J=9 Hz), 7.05 (4H, d, J=9 Hz), 6.68 (2H, d, J=8.5 Hz), 6.05 (1H, m), 5.42-5.39 (2H, m), 4.66 (2H, d, J=8.5 Hz), 4.15 (2H, S). $^{13}$Carbon ($^{13}$C) NMR spectrum (CDCl$_3$, 500 megahertz (MHz)): δ 196.9, 162.4, 156.5, 133.5, 131.2, 130.8, 129.7, 125.7, 118.3, 115.6, 115, 68.8, 44.

The monoallyl-deoxybenzoin, shown as compound 8 in FIG. 9, was synthesized by heating compound 7 to 190° C. for 18 hours in a nitrogen atmosphere, then cooling to ambient temperature.

Figure 10:
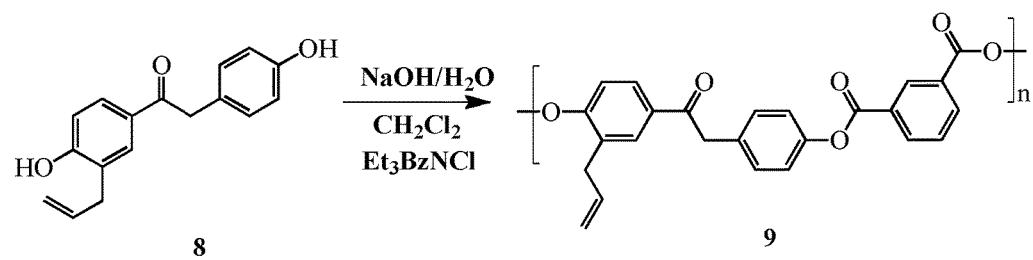
FIG. 10 is a chemical scheme illustrating the polymerization of the monoallyl-functionalized bisphenolic deoxybenzoin.

An exemplary polymerization procedure for producing aromatic polyesters from monoallyl-BHDB (7) is illustrated by FIG. 10.

Example 6

Figure 11:
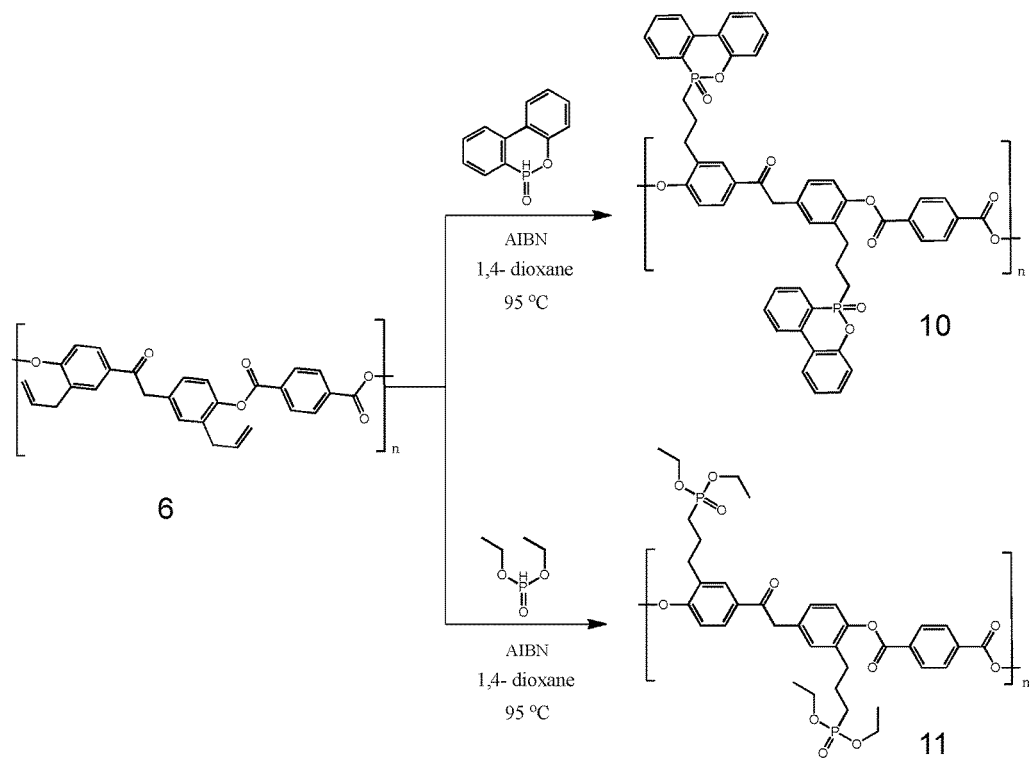
FIG. 11 is a chemical scheme illustrating the post-polymerization functionalization of the diallyl-BHDB polyester with various phosphites.

Post-polymerization modification of polymer 6 was demonstrated using 9,10-Dihydro-9-oxa-10-phosphaphenanthrene 10-oxide (DOPO), as shown in FIG. 11. Experimental details follow.

To a solution of diallyl-containing polymer (6) ($M_n$=16,000 Da, PDI 2.7) (0.25 grams) in dry 1,4-dioxane was added dihydro-9-oxa-10-phosphaphenathrene (DOPO) (0.5 grams, 2.2 millimoles) followed by addition of azobisisobutyronitrile (AIBN) (20 milligrams, 5 mole percent). The reaction mixture was stirred at 90° C. for 12 hours. The mixture was then cooled to room temperature and the polymer was precipitated by addition of excess methanol (3×100 milliliters). The solid was filtered then dried in a vacuum oven at 60° C. for 12 hours to provide the DOPO-functionalized polymer, shown as polymer 10 in FIG. 11. An analogous procedure can be used to prepare the corresponding diethyl phosphite derivative, shown as polymer 11 in FIG. 11.

Example 7

Experimental details for the synthesis of a dipropargyl-bishydroxydeoxybenzoin are provided below.

Figure 12:
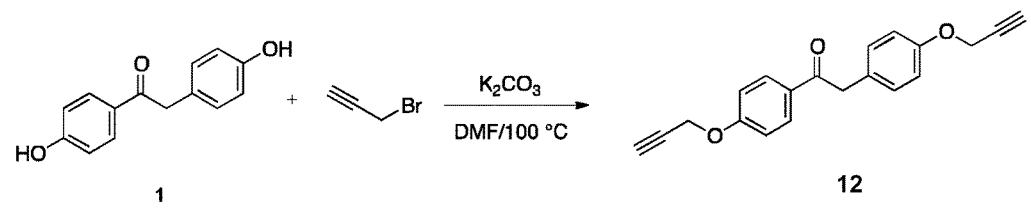
FIG. 12 is a chemical scheme illustrating the synthesis of a dipropargyl ether-functionalized deoxybenzoin.

The dipropargyl ether of BHDB, shown as compound 12 in FIG. 12, was prepared according to the following synthetic procedure. Potassium carbonate (3.6 grams, 26 millimoles) was placed into a 500 milliliter round bottom flask, to which was added BHDB (2.00 grams, 8.76 millimoles) and dimethyl formamide (17 milliliters). The resulting mixture was cooled to 0° C. and propargyl bromide (1.98 milliters, 26.0 millimoles) was added slowly. The mixture was heated to 100° C. and kept overnight at this temperature, then cooled and extracted with chloroform and water. The organic layer was washed with brine and passed through magnesium sulfate, and the product was obtained following evaporation of solvent then crystallization from methanol. Compound 12 was characterized by proton ($^1$H) and carbon ($^{13}$C) NMR spectroscopy in deuterated chloroform. The chemical shifts are reported in parts per million (ppm) relative to tetramethyl silane (TMS) as a reference. $^1$H-NMR (300 MHz, CDCl$_3$): δ 8.04 (d, 2H, Ar—H), 7.23 (d, 2H, Ar—H), 7.07 (d, 2H, Ar—H), 6.97 (d, 2H, Ar—H), 4.69-4.77 (m, 4H, Ar—O—CH$_2$), 4.20 (s, 2H, Ar—CH$_2$—CO—Ar), 2.57 (m, 2H, acetylene-H); $^{13}$C NMR (300 MHz, CDCl$_3$): δ 196.08, 161.36, 156.44, 130.36, 127.78, 115.06, 55.81, 44.17.

The invention includes at least the following embodiments, which are non-limiting.

Embodiment 1

An unsaturated deoxybenzoin compound having the structure (I), (II), or (III)

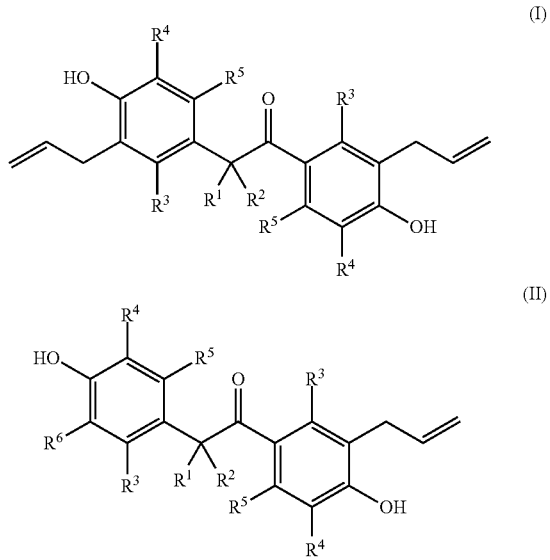

-continued

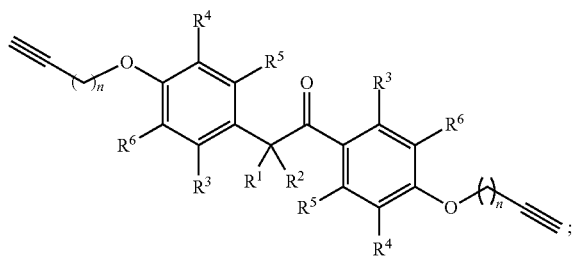

wherein $R^1$ and $R^2$ are independently at each occurrence hydrogen, a halogen, a nitrile group, a $C_{1-6}$ alkyl group, or a $C_{6-20}$ aryl group; $R^3$, $R^4$, $R^5$, and $R^6$ are independently at each occurrence hydrogen, a halogen, a hydroxyl group, a nitrile group, a $C_{1-6}$ alkyl group, a $C_{1-6}$ alkoxy group, or a $C_{6-20}$ aryl group; and n is independently at each occurrence an integer from 1 to 12.

Embodiment 2

The deoxybenzoin compound of embodiment 1, wherein each occurrence of $R^1$ and $R^2$ is hydrogen.

Embodiment 3

The deoxybenzoin compound of embodiment 1 or 2, wherein each occurrence of n is 1.

Embodiment 4

The deoxybenzoin compound of any of embodiments 1 to 3, wherein each occurrence of $R^3$, $R^4$, $R^5$, and $R^6$ is hydrogen.

Embodiment 5

The deoxybenzoin compound of any of embodiments 1 to 4, wherein the deoxybenzoin compound has the structure (I)

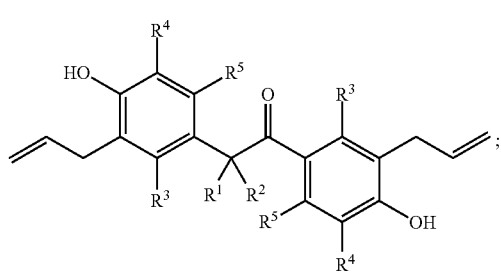

each occurrence of $R^1$ and $R^2$ is hydrogen; and each occurrence of $R^3$, $R^4$, and $R^5$ is hydrogen.

Embodiment 6

The deoxybenzoin compound of any of embodiments 1 to 4, wherein the deoxybenzoin compound has the structure (II)

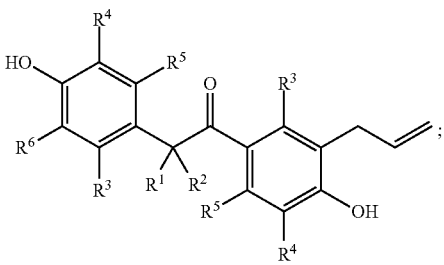

each occurrence of $R^1$ and $R^2$ is hydrogen; and each occurrence of $R^3$, $R^4$, $R^5$, and $R^6$ is hydrogen.

Embodiment 7

The deoxybenzoin compound of any of embodiments 1 to 4, wherein the deoxybenzoin compound has the structure (III)

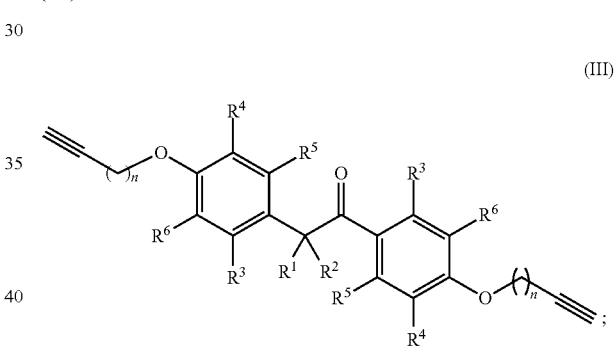

each occurrence of $R^1$ and $R^2$ is hydrogen; each occurrence of n is 1; and each occurrence of $R^3$, $R^4$, $R^5$, and $R^6$ is hydrogen.

Embodiment 8

A polyester comprising repeating units having the structure (IV), (V), or a combination thereof

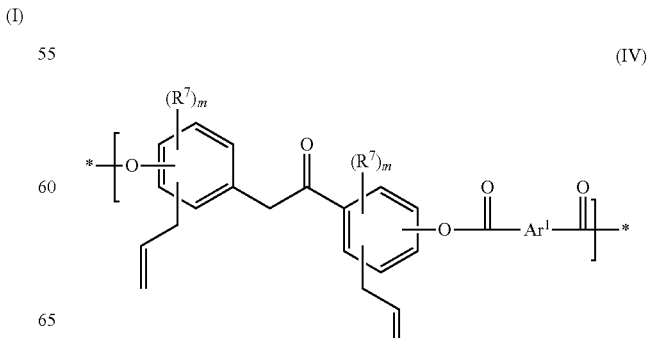

-continued

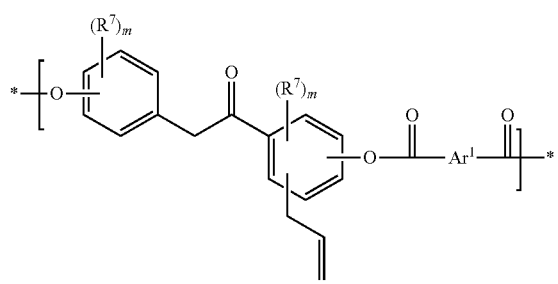

(V)

wherein $Ar^1$ is a divalent substituted or unsubstituted $C_{6-20}$ arylene group; $R^7$ is independently at each occurrence a halogen, a hydroxyl group, a nitrile group, a $C_{1-6}$ alkyl group, a $C_{1-6}$ alkoxy group, or a $C_{6-20}$ aryl group; and m is independently at each occurrence 0, 1, 2, 3, or 4.

Embodiment 9

The polyester of embodiment 8, wherein $Ar^1$ is a phenylene group.

Embodiment 10

The polyester of embodiment 8 or 9, wherein m is 0.

Embodiment 11

The polyester of any of embodiments 8 to 10, wherein the polyester comprises repeating units having the structure (IV).

Embodiment 12

The polyester of any of embodiments 8 to 10, wherein the polyester comprises repeating units having the structure (V).

Embodiment 13

The polyester of any of embodiments 8 to 12, wherein the polyester is a copolyester further comprising repeating units derived from a dihydroxy compound of the formula

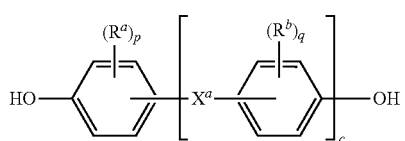

wherein $R^a$ and $R^b$ are each independently a halogen atom or a $C_{1-6}$ alkyl group; p and each occurrence of q are each independently 0, 1, 2, 3, or 4; c is 0, 1, 2, 3, or 4; and $X^a$ is a single bond, —O—, —S—, —S(O)—, —SO$_2$—, —C(O)—, or a $C_{1-18}$ hydrocarbylene group.

Embodiment 14

The polyester of any of embodiments 8 to 13, wherein the polyester is a copolyester further comprising repeating units derived from bisphenol A.

Embodiment 15

The polyester of any of embodiments 8 to 14, wherein the polyester has a number average molecular weight of 1,000 to 100,000 Daltons.

Embodiment 16

The polyester of embodiment 8, wherein the polyester has repeating units of formula (VI)

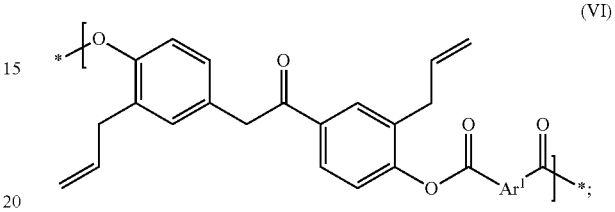

(VI)

$Ar^1$ is a phenylene group; and the polyester has a molecular weight of 10,000 to 100,000 Daltons.

Embodiment 17

The polyester of embodiment 8, wherein the polyester is a copolyester comprising repeating units of formulas (VI) and (VII)

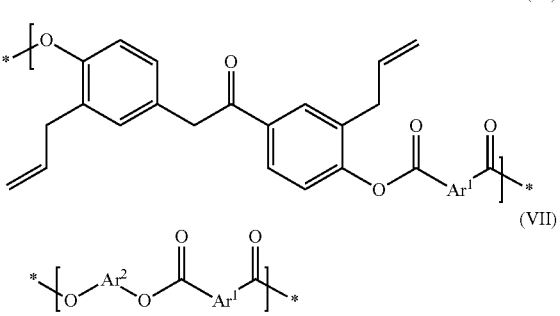

(VI)

(VII)

$Ar^1$ is phenylene; $Ar^2$ is 4,4'-diphenylene isopropylidene; and the polyester has a molecular weight of 10,000 to 100,000 Daltons.

Embodiment 18

The polyester of embodiment 8, wherein the polyester has repeating units of formula (VIII)

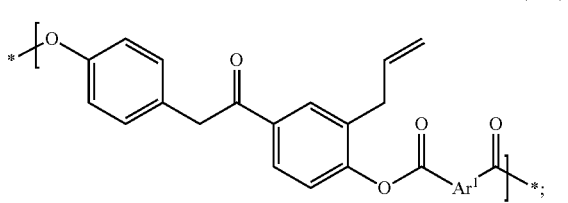

(VIII)

$Ar^1$ is a phenylene group; and the polyester has a molecular weight of 10,000 to 100,000 Daltons.

Embodiment 19

The polyester of embodiment 8, wherein the polyester is a copolyester comprising repeating units of formulas (VIII) and (VII)

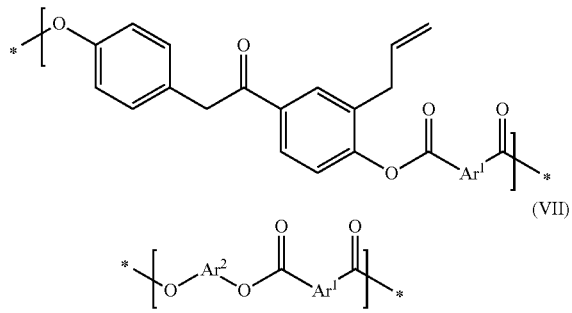

(VIII)

(VII)

$Ar^1$ is phenylene; $Ar^2$ is 4,4'-diphenylene isopropylidene; and the polyester has a molecular weight of 10,000 to 100,000 Daltons.

Embodiment 20

The polyester of any of embodiments 8 to 19, wherein the polyester exhibits one or more of the following properties: a five percent weight loss temperature of greater than or equal to 350° C., as determined using thermogravimetric analysis; a char yield of at least 35 percent after 60 minutes at 750° C., as determined by thermogravimetric analysis; a heat release capacity of less than or equal to 150 joules per gram-Kelvin determined using a pyrolysis combustion flow calorimeter; and a total heat release of less than 15 kilojoules per gram determined using a pyrolysis combustion flow calorimeter.

Embodiment 21

A polyester comprising repeating units having the structure (IX), (X), or a combination thereof

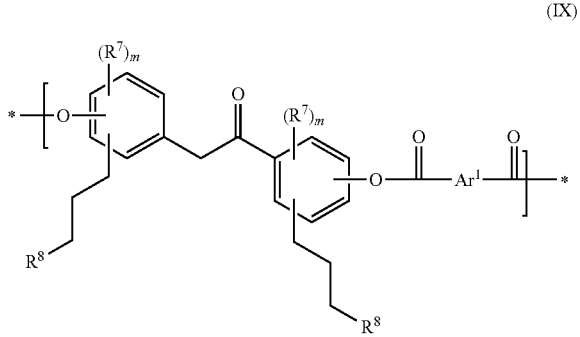

(IX)

(X)

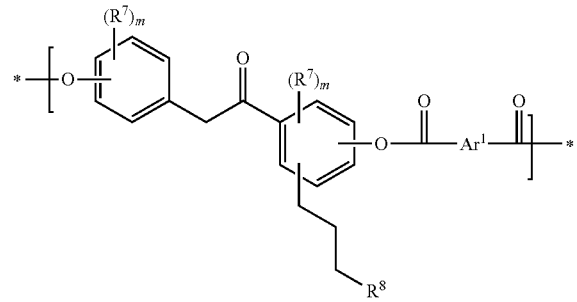

wherein $Ar^1$ is a divalent substituted or unsubstituted $C_{6-20}$ arylene group; $R^7$ is independently at each occurrence a halogen, a hydroxyl group, a nitrile group, a $C_{1-6}$ alkyl group, a $C_{1-6}$ alkoxy group, or a $C_{6-20}$ aryl group; m is independently at each occurrence 0, 1, 2, 3, or 4; and $R^8$ is a phosphorous-containing group.

Embodiment 22

The polyester of embodiment 21, wherein $R^8$ is independently at each occurrence

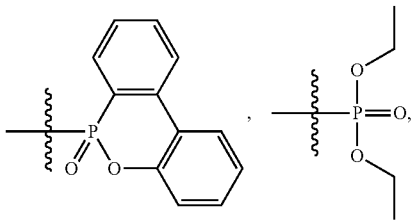

or a combination thereof.

Embodiment 23

An article comprising the polyester of any of embodiments 8 to 22.

Embodiment 24

The article of embodiment 23, wherein the article is a fiber, textile, a furniture component, an adhesive, a foam, paint, or a plastic.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety, including priority U.S. Patent Application No. 62/238,186, filed Oct. 7, 2015. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or" unless clearly indicated otherwise. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

As used herein, the term "hydrocarbyl" and "hydrocarbylene" mean a monovalent or divalent, respectively, group containing carbon, hydrogen, and optionally one or more heteroatoms (e.g., 1, 2, 3, or 4 atoms such as halogen, O, N, S, P, or Si). "Alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene ($-CH_2-$) or propylene ($-(CH_2)_3-$)). "Alkenyl" and "alkenylene" mean a monovalent or divalent, respectively, straight or branched chain hydrocarbon group having at least one carbon-carbon double bond (e.g., ethenyl ($-HC=CH_2$) or propenylene ($-HC(CH_3)=CH_2-$). "Alkynyl" means a straight or branched chain, monovalent hydrocarbon group having at least one carbon-carbon triple bond (e.g., ethynyl). "Alkoxy" means an alkyl group linked via an oxygen (i.e., alkyl-O—), for example methoxy, ethoxy, and sec-butyloxy. "Cycloalkyl" and "cycloalkylene" mean a monovalent and divalent cyclic hydrocarbon group, respectively, of the formula $-C_nE_{2n-x}$ and $-C_nE_{2n-2x}-$ wherein x is the number of cyclization(s). "Aryl" means a monovalent, monocyclic or polycyclic aromatic group (e.g., phenyl or naphthyl). "Arylene" means a divalent, monocyclic or polycyclic aromatic group (e.g., phenylene or naphthylene). The prefix "halo" means a group or compound including one more halogen (F, Cl, Br, or I) substituents, which can be the same or different. The prefix "hetero" means a group or compound that includes at least one ring member that is a heteroatom (e.g., 1, 2, or 3 heteroatoms, wherein each heteroatom is independently N, O, S, or P.

"Substituted" means that the compound or group is substituted with at least one (e.g., 1, 2, 3, or 4) substituents instead of hydrogen, where each substituent is independently nitro ($-NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g, benzyl), $C_{7-12}$ alkylarylene (e.g, toluyl), $C_{4-12}$ heterocycloalkyl, $C_{3-12}$ heteroaryl, $C_{1-6}$ alkyl sulfonyl ($-S(=O)_2$-alkyl), $C_{6-12}$ arylsulfonyl ($-S(=O)_2$-aryl), or tosyl ($CH_3C_6H_4SO_2-$), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

The invention claimed is:

1. An unsaturated deoxybenzoin compound having the structure (I), (II), or (III)

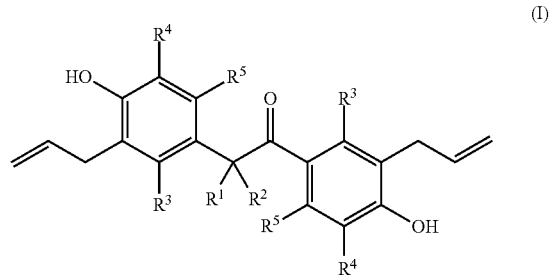

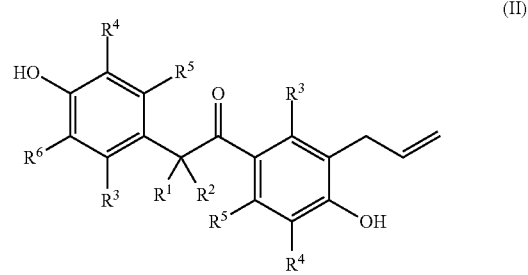

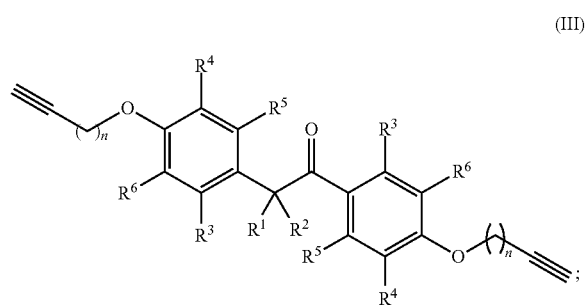

wherein $R^1$ and $R^2$ are independently at each occurrence hydrogen, a halogen, a nitrile group, a $C_{1-6}$ alkyl group, or a $C_{6-20}$ aryl group;

$R^3$, $R^4$, $R^5$, and $R^6$ are independently at each occurrence hydrogen, a halogen, a hydroxyl group, a nitrile group, a $C_{1-6}$ alkyl group, a $C_{1-6}$ alkoxy group, or a $C_{6-20}$ aryl group; and n is independently at each occurrence an integer from 1 to 12.

2. The deoxybenzoin compound of claim 1, wherein each occurrence of $R^1$ and $R^2$ is hydrogen.

3. The deoxybenzoin compound of claim 1, wherein each occurrence of n is 1.

4. The deoxybenzoin compound of claim 1, wherein each occurrence of $R^3$, $R^4$, $R^5$, and $R^6$ is hydrogen.

5. The deoxybenzoin compound of claim 1, wherein
the deoxybenzoin compound has the structure (I)

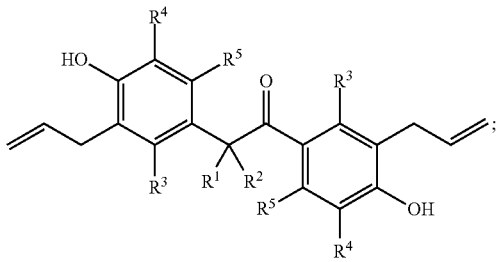

each occurrence of $R^1$ and $R^2$ is hydrogen; and
each occurrence of $R^3$, $R^4$, and $R^5$ is hydrogen.

6. The deoxybenzoin compound of claim 1, wherein
the deoxybenzoin compound has the structure (II)

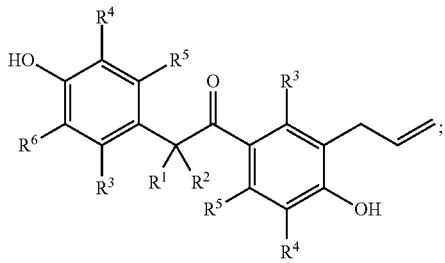

each occurrence of $R^1$ and $R^2$ is hydrogen; and
each occurrence of $R^3$, $R^4$, $R^5$, and $R^6$ is hydrogen.

7. The deoxybenzoin compound of claim 1, wherein the deoxybenzoin compound has the structure (III)

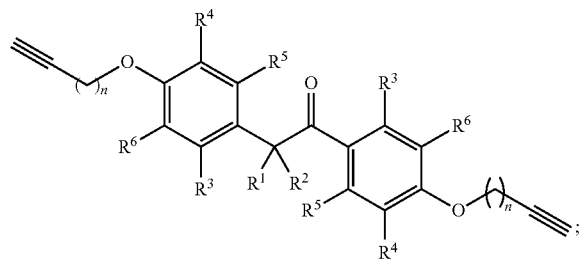

each occurrence of $R^1$ and $R^2$ is hydrogen;
each occurrence of n is 1; and
each occurrence of $R^3$, $R^4$, $R^5$, and $R^6$ is hydrogen.

8. A polyester comprising repeating units having the structure (IV), (V), or a combination thereof

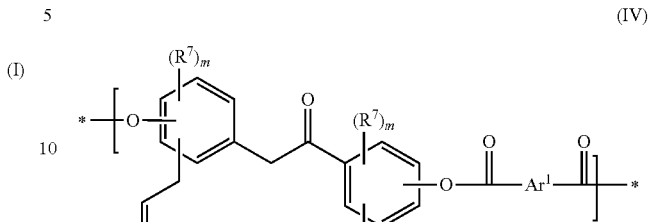

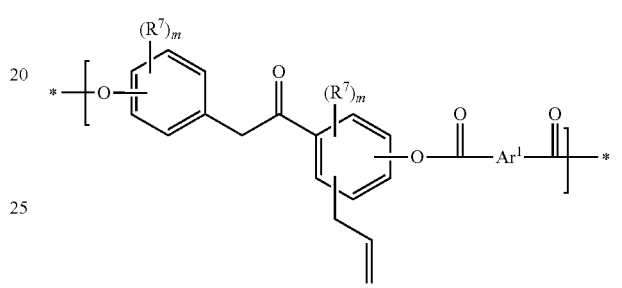

wherein
Ar$^1$ is a divalent substituted or unsubstituted $C_{6-20}$ arylene group;
$R^7$ is independently at each occurrence a halogen, a hydroxyl group, a nitrile group, a $C_{1-6}$ alkyl group, a $C_{1-6}$ alkoxy group, or a $C_{6-20}$ aryl group; and
m is independently at each occurrence 0, 1, 2, 3, or 4.

9. The polyester of claim 8, wherein Ar$^1$ is a phenylene group.

10. The polyester of claim 8, wherein m is 0.

11. The polyester of claim 8, wherein the polyester is a copolyester further comprising repeating units derived from a dihydroxy compound of the formula

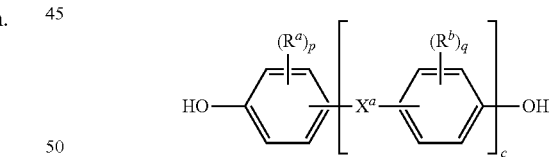

wherein
$R^a$ and $R^b$ are each independently a halogen atom or a $C_{1-6}$ alkyl group;
p and each occurrence of q are each independently 0, 1, 2, 3, or 4;
c is 0, 1, 2, 3, or 4; and
$X^a$ is a single bond, —O—, —S—, —S(O)—, —SO$_2$—, —C(O)—, or a $C_{1-18}$ hydrocarbylene group.

12. The polyester of claim 8, wherein the polyester is a copolyester further comprising repeating units derived from bisphenol A.

13. The polyester of claim 8, wherein the polyester has a number average molecular weight of 1,000 to 100,000 Daltons.

14. The polyester of claim 8, wherein
the polyester has repeating units of formula (VI)

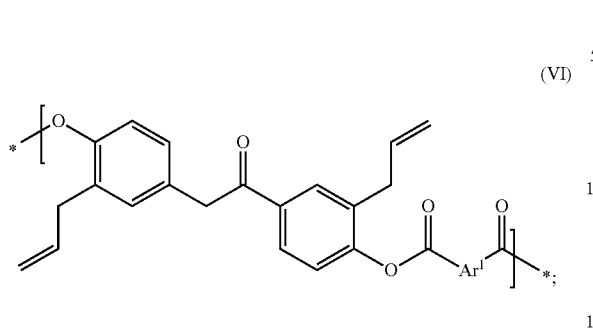
(VI)

Ar¹ is a phenylene group; and
the polyester has a molecular weight of 10,000 to 100,000 Daltons.

15. The polyester of claim 8, wherein
the polyester is a copolyester comprising repeating units of formulas (VI) and (VII)

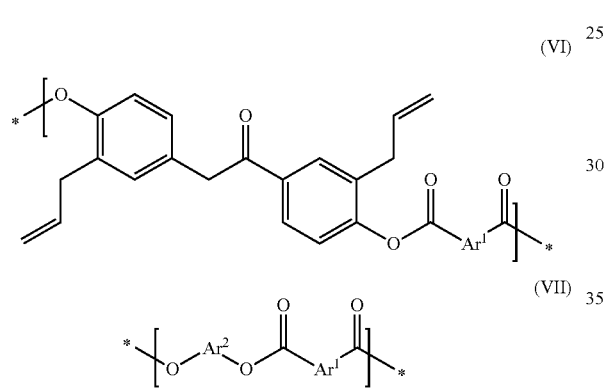
(VI)

(VII)

Ar¹ is phenylene;
Ar² is 4,4'-diphenylene isopropylidene; and
the polyester has a molecular weight of 10,000 to 100,000 Daltons.

16. The polyester of claim 8, wherein
the polyester has repeating units of formula (VIII)

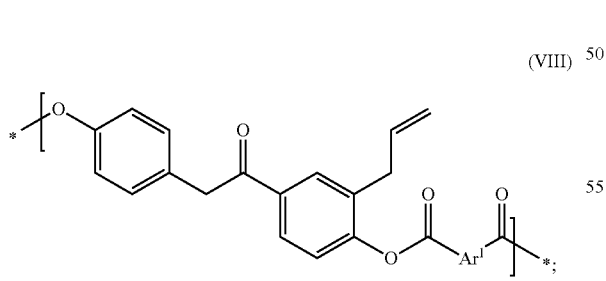
(VIII)

Ar¹ is a phenylene group; and
the polyester has a molecular weight of 10,000 to 100,000 Daltons.

17. The polyester of claim 8, wherein
the polyester is a copolyester comprising repeating units of formulas (VIII) and (VII)

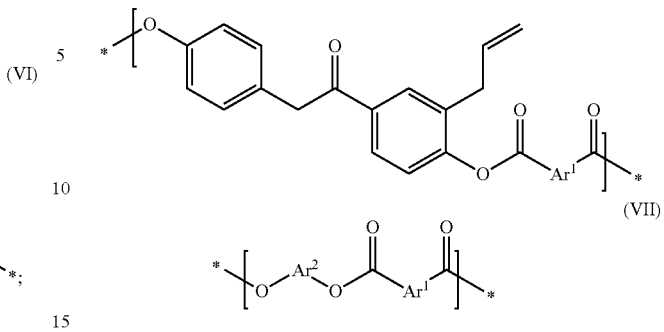
(VIII)

(VII)

Ar¹ is phenylene;
Ar² is 4,4'-diphenylene isopropylidene; and
the polyester has a molecular weight of 10,000 to 100,000 Daltons.

18. The polyester of claim 8, wherein the polyester exhibits one or more of the following properties:
a five percent weight loss temperature of greater than or equal to 350° C., as determined using thermogravimetric analysis;
a char yield of at least 35 percent after 60 minutes at 750° C., as determined by thermogravimetric analysis;
a heat release capacity of less than or equal to 150 joules per gram-Kelvin determined using a pyrolysis combustion flow calorimeter; and
a total heat release of less than 15 kilojoules per gram determined using a pyrolysis combustion flow calorimeter.

19. A polyester comprising repeating units having the structure (IX), (X), or a combination thereof

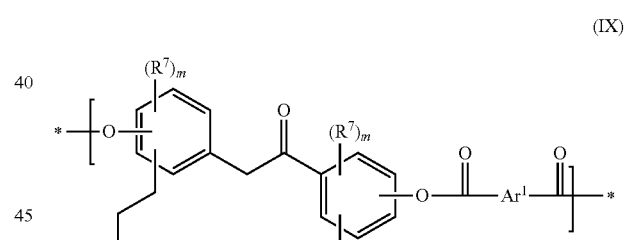
(IX)

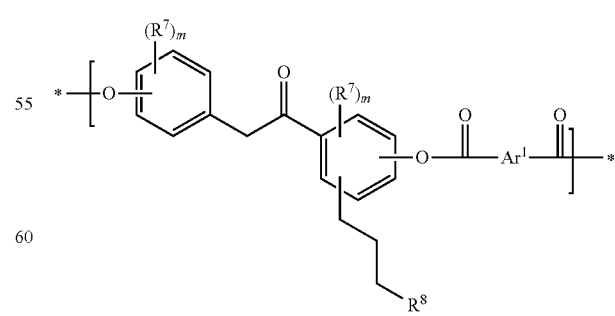
(X)

wherein
Ar¹ is a divalent substituted or unsubstituted $C_{6\text{-}20}$ arylene group;

R⁷ is independently at each occurrence a halogen, a hydroxyl group, a nitrile group, a $C_{1-6}$ alkyl group, a $C_{1-6}$ alkoxy group, or a $C_{6-20}$ aryl group;
m is independently at each occurrence 0, 1, 2, 3, or 4; and
R⁸ is a phosphorous-containing group.
20. The polyester of claim 19, wherein R⁸ is independently at each occurrence
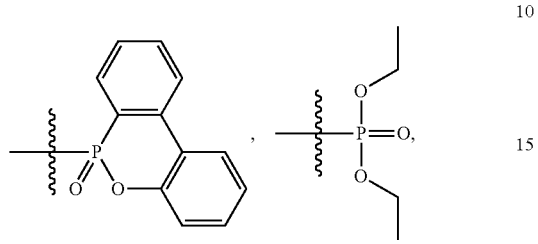
or a combination thereof.
* * * * *